United States Patent [19]

Newman et al.

[11] Patent Number: 4,885,399
[45] Date of Patent: Dec. 5, 1989

[54] PROCESS FOR OBTAINING SUBSTANTIALLY ALDEHYDE-FREE KETONE PRODUCTS

[75] Inventors: Stanley F. Newman, Walnut Creek; Jacques C. De Deken, Palo Alto; Michael L. Cook, Sunnyvale, all of Calif.

[73] Assignee: Catalytica, Inc., Mountain View, Calif.

[21] Appl. No.: 218,693

[22] Filed: Jul. 13, 1988

Related U.S. Application Data

[63] Continuation-in-part of Ser. No. 120,683, Nov. 12, 1987, abandoned, which is a continuation of Ser. No. 935,281, Nov. 26, 1986, abandoned.

[51] Int. Cl.$^4$ .................................................. C07C 45/85
[52] U.S. Cl. ..................................... 568/410; 568/411; 568/400; 568/401
[58] Field of Search ................ 568/400, 401, 410, 411

[56] References Cited

U.S. PATENT DOCUMENTS

| | | | |
|---|---|---|---|
| 1,700,103 | 1/1929 | Van Schaack | 568/388 |
| 2,487,124 | 11/1949 | Gathman | 5689/411 |
| 3,198,837 | 8/1965 | Smidt | 568/410 |
| 3,392,200 | 7/1968 | Vrbaski | 568/411 |
| 3,461,157 | 8/1969 | Olivier et al. | 568/401 |
| 3,668,257 | 6/1972 | Schaeffer | 568/401 |
| 3,822,318 | 7/1974 | Brownstein | 568/400 |
| 3,839,456 | 10/1974 | Royston | 568/400 |
| 3,932,521 | 1/1976 | Gloyer | 568/400 |
| 4,203,927 | 5/1980 | Stapp | 568/401 |
| 4,329,510 | 5/1982 | Uno | 568/411 |
| 4,419,525 | 12/1983 | Shioyama | 568/401 |
| 4,507,507 | 3/1985 | Murtha | 568/401 |
| 4,720,474 | 1/1988 | Vasilevskis | 568/401 |
| 4,723,041 | 2/1988 | Vasilevskis | 568/401 |

FOREIGN PATENT DOCUMENTS

| | | | |
|---|---|---|---|
| 501374 | 4/1954 | Canada | 568/410 |
| 45-39083 | 12/1970 | Japan | 568/410 |
| 47-33323 | 8/1972 | Japan | 568/410 |
| 56-158725 | 12/1981 | Japan | 568/411 |
| 58-208246 | 12/1983 | Japan | 568/411 |

OTHER PUBLICATIONS

Smidt J. and Krekeler H. 6th World Petroleum Congress, Section IV, Paper 40-PD9, Frankfurt, 1963).
Hydrocarbon Processing, 204, Nov., 1969.
Stewart T. D. and Donally L. H., Journal of the American Chemical Society, 54, 2333, 3555, 3359 (1932).
Sorensen P. E. and Anderson V. S., Acta Chemica Scandinavia, 24, 1301 (1970).
Lin I. and Day A. R., "A Study of Mixed Tischtschenko Reaction," J. Amer. Chem. Soc., 74, 5133, (1952).

(List continued on next page.)

*Primary Examiner*—James H. Reamer
*Attorney, Agent, or Firm*—Limbach, Limbach & Sutton

[57] ABSTRACT

Tischtschenko condensation of aldehydes is used to remove aldehydes from dry ketone-containing streams. The tischtschenko condensation is used to condense the aldehydes into esters whose boiling points are significantly different than the ketones, greatly simplifying the separation of the esters from the ketones. An organic extraction step is used to obtain a substantially dry ketone containing stream. One particularly preferred class of extraction solvents is selected from the group consisting of butane, pentane, hexane, heptane, octane, nonane, decane and mixtures thereof. In particularly preferred embodiments, the Tischtschenko reaction is used in the context of aqueous-phase catalyzed olefin oxidation to ketones. The aldehyde to ester condensation permits easy and efficient removal of the aldehyde analogs of the desired ketones.

62 Claims, 7 Drawing Sheets

OTHER PUBLICATIONS

W. C. Child and H. Adkins, "The Condensation of Aldehydes to Ester by Aluminum Ethoxide," J. Amer. Chem. Soc., 45, 3013 (Dec. 1923).

W. C. Child and H. Adkins, "The Condensation of Aldehydes to Ester by Alkoxides," J. Amer. Chem. Soc., 47, 798 (Mar. 1925).

M. S. Kulpinski and F. F. Nord, "New Synthesis of Glycol Esters" J. Org. Chem., 8, 256–70 (1943).

F. J. Villani and F. F. Nord, "Glycol Esters form Aldehydes," J. Amer. Chem. Soc., 68, 1674 (1946).

Chemical Engineering News, "Wacker Process Can Make Acetone" vol. 50, Jul. 8, 1963.

W. L. McCabe and J. C. Smith, Unit Operations of Chemical Engineering, Chapter 20, (McGraw-Hill, 1976).

R. Treybal, Mass Transfer Operations, Chapter 10, (McGraw-Hill), 1963, pp. 477–561.

R. H. Perry and C. H. Chilton, Chemical Engineers' Handbook, 5th Ed., Section 21 (McGraw-Hill), 1973.

R. E. Treybal, O. J. Vondrak, Industrial & Engineering Chemistry, vol. 41, No. 8, pp. 1761–1763, Aug., 1949.

PROCESS FOR OBTAINING SUBSTANTIALLY ALDEHYDE-FREE KETONE PRODUCTS

RELATED APPLICATION DATA

This application is a continuation in part application of our commonly owned, co-pending application Ser. No. 120,683, filed Nov. 12, 1987 now abandoned, which is a continuation of No. 935,281, now abandoned, filed Nov. 26, 1986.

TECHNICAL FIELD

This invention relates generally to the separation of aldehydes from ketones. More specifically, the present invention is directed to a process in which an aldehyde condensation reaction is used to remove undesirable aldehydic impurities from the desired ketone by the formation of higher boiling ester products. This process has specific application in the manufacture of ketones via olefin oxidation reactions.

BACKGROUND OF THE INVENTION

Oxidation of alkenes or alkanes to ketones often produces crude ketone streams that contain variable amounts of aldehyde byproducts, among others. These aldehyde byproducts need to be removed from the crude ketone streams to meet the product specifications, of purity and/or odor, of the end product.

According to the prior art, the removal of aldehydes from ketones is commonly achieved in one of the following two ways: (1) by direct separation, using an appropriate physical unit operation, such as thermal distillation or physical adsorption; or, (2) by converting the aldehyde into a product which is more amenable to separation from the ketone than the parent aldehyde, followed by an appropriate separation of the reaction product. The latter approach typically involves the use of a chemical reaction, such as hydrogenation, aldol condensation or bisulfite adduction, and is especially preferred, if not required, when the physical properties of the aldehyde impurity and the desired ketone (such as boiling point or molecular size) are too similar to enable an economical direct separation (such as distillation).

Examples of the above methods for removing aldehydes from ketones that have been disclosed in the literature include: physical adsorption of the aldehyde on activated alumina or molecular sieves (Japanese Pat. No. J45-39083); hydrogenation of the aldehyde into the corresponding alcohol followed by distillation (Smidt J. and Krekeler H., 6th World Petroleum Congress, Section IV, Paper 40-PD9, Frankfurt, 1963); aldol condensation of the aldehyde into an aldol product followed by, or integrated with, distillation (U.S. Pat. No. 3,198,837; U.S. Pat. No. 3,392,200; Japanese Pat. No. J56-158725; U.S. Pat. No. 4,329,510; Japanese Patent No. J58-208246); and addition of the aldehyde to sodium bisulfite followed by removal of the bisulfite adduct (Hydrocarbon Processing, 204, November, 1969; Japanese Pat. No. J47-33323; Stewart T. D. and Donally L. H., Journal of the American Chemical Society, 54, 2333, 3555, 3559, 1932; Sorensen P. E. and Andersen V. S., Acta Chemica Scandinavia, 24, 1301, 1970).

In commercial application, ketone products often have rigorous odor specifications, which require the elimination of substantially all aldehydic impurities which are oderiferous themselves or are the precursors of readily formed oderiferous compounds. As a result, final, commercial ketone product specifications often require that aldehydic impurities be present in the ketone only at the parts per million level. Economic separation of aldehyde(s) from ketone(s) by one of the above methods to meet these specifications is often very difficult. These methods all rely on a physical or chemical operation which is not specific for the aldehyde, and which thereby affects the ketone. These methods therefore typically result in economically unacceptable losses of the desired ketone. The dramatic selectivity requirements imposed on these physical or chemical operations, to achieve an economical removal of the aldehyde from the ketone, is best illustrated by the following example.

In this example, it is assumed that the removal operation (either physical adsorption or chemical reaction) has first order kinetics in both the aldehyde and the ketone. The integrated continuity equations for a batch or plug flow reactor, and backmixed operation respectively, are written:

$$\text{PLUG FLOW:} \quad \left(\frac{100-b}{100}\right)^{k_A/k_K - 1} = \frac{(100-a)}{a} \cdot \frac{c}{(10^6 - c)}$$

$$\text{BACKMIXING:} \quad (k_A/k_K - 1) \cdot b = \frac{100 \cdot a}{(100-a)} \cdot \frac{(10^6 - c)}{c} - 100$$

where: $a$ = wt. % of aldehyde in the crude ketone feed,
$b$ = wt. % loss of ketone,
$c$ = residual aldehyde concentration, ppm
$k_A$ = aldehyde first order "rate" constant, $hr^{-1}$
$k_K$ = ketone first order "rate" constant, $hr^{-1}$ These equations, which allow one to calculate the required $k_A/k_K$ ratio for given values of $a$ and $c$, and desired value of $b$, are illustrated in FIG. 1 ( batch or plug flow operation) and FIG. 2 (backmixed operation) for a ketone feed which contains 1 wt. % aldehyde. These figures show that, in order to achieve 50 ppm residual aldehyde in the final ketone product at less than 5 wt. % loss of the desired ketone, a kinetic selectivity ratio $(k_A/k_K)$ in excess of 100 is needed in the case of batch or plug flow operation. A kinetic selectivity ratio $k_A/k_K$ close to 5000 is desirable for the backmixed operation. These numbers suggest that the removal operation is best carried out in plug flow mode, and explain why an aldehyde specific ($k_A/k_K$ = infinity) operation would be most preferred to obtain the minimum loss of ketone.

Thus, in selecting a method for aldehyde removal, it is important that the method be highly selective, if not entirely specific towards the aldehyde, to minimize ketone loss. The requirement of high selectivity in the aldehyde is especially difficult to meet when the aldehyde is of same molecular weight as the desired ketone. None of the above-described common methods for aldehyde removal appears to be adequately selective in practice to be commercially viable.

In contrast with the above prior art methods for aldehyde separation from ketones, the use of a Tischtschenko condensation of the aldehyde into a higher boiling ester product, followed by overhead distillation of the ketone to separate it from the high boiling ester product, is particularly well suited to separating aldehydic impurities from ketones, since this reaction provides substantially higher reaction selectivity. The carbonyl group of ketones does not have alpha-hydrogen atoms attached to the carbon atom; therefore, ketones cannot undergo the Tischtschenko reaction. In contrast with the above described prior art methods for aldehyde separation from ketones, the Tischtschenko condensation of aldehyde containing ketones is, therefore, anticipated to be highly selective, if not specific, toward the aldehyde.

While, in the preferred embodiments of this invention, this method may be advantageously applied to purification of ketones produced via olefin oxidation in the presence of precious metal catalysts, the selective condensation of aldehydes in the presence of ketones is more generally applied. It finds independent value in ketone production and purification via other reaction routes, such as the direct oxidation of alkanes (e.g., butane oxidation to methyl ethyl ketone and acetic acid). Also, while it is a specific intent to remove aldehydic impurities from desired ketones, the method of the present invention also applies to aldehyde/ketone streams in which the aldehyde concentration exceeds impurity-level concentrations, for example up to 10 wt. % aldehyde concentration or more.

One limitation of the present invention is that Tischtschenko condensation catalysts require substantially dry crude ketone streams to efficiently condense contained aldehydic components into heavier (and more easily separable) ester products. This limitation, however, is not overly limiting since various methods are available to create a dry, ketone-rich stream from a wet, ketone-rich stream. Among them are thermal distillation, azeotropic distillation, salting out the ketone from water by saturating the system with a salt such as sodium chloride or calcium chloride, as well as combinations of these methods. Adsorption of the water on drying agents such as molecular sieves can be used. As explained more fully below, extraction of the ketone and aldehydes with an organic solvent has been found to be an efficient "drying" method. Extraction is effective, economic, and easily integrated into a total ketone manufacturing process. Suitable extraction solvents for obtaining dry ketone streams will be those solvents having low miscibility with water and in which the ketone product is highly soluble. Such solvents include alkanes, cycloalkanes, aromatics, and their chlorinated derivatives.

One prior art reaction scheme for making ketones via partial olefin oxidation is the Wacker process. (See Chemical Engineering News, Vol. 50, July 8, 1963.) In the Wacker process, catalyzed by palladium salts, cupric chloride is utilized as the oxidizing agent in a stoichiometric manner, with the resulting cuprous chloride being subsequently reoxidized in a separate reactor (a one-stage reactor scheme). In another version of the Wacker process also using a palladium salt catalyst, oxygen is co-fed with the olefin and the aqueous catalyst solution, so that the cuprous chloride is continuously reoxidized to cupric chloride, thus using the cupric chloride in a catalytic manner (a one-stage reactor scheme). Alternatively, reduced chloride systems are described in Murtha U.S. Pat. No. 4,507,507, and in our U.S. Pat. No. 4,720,474 and Vasilevskis et al U.S. Pat. No. 4,723,041.

Regardless of which of these olefin oxidation processes is used to obtain ketones, a common characteristic of these systems is the makeup of the oxidation reaction mass, or corresponding crude ketone product mixture. Typically, this crude ketone product mixture, subsequent to the oxidation reaction, consists of an aqueous phase containing a palladium catalyst and all, or part of the ketone product. In addition, a ketone-rich organic phase containing unreacted feed components and other oxidation process components (diluents, surfactants, etc.) will form if the ketone concentration exceeds solubility limits in the aqueous phase. The crude ketone product will generally contain as impurities: water, an aldehyde of the same molecular weight as the ketone, organic acids, and other olefin oxidation products.

If the ketone is obtained via olefin oxidation in an aqueous medium, such as in the Wacker process, it is necessary to recover the desired ketone from the crude oxidation reaction mass, including the dissolved catalyst components. Further, efficient and economic recovery and purification of the ketone product made via such aqueous phase olefin oxidation may be complicated by formation of ketone/water azeotropes, making application of simple thermal distillation techniques impractical to separate the desired ketone, the aqueous phase and other organic oxidation reaction byproducts.

Important olefin oxidation process economics factors affect the separation of the desired ketone products from the crude ketone product. Quantitative recovery of any precious metal catalyst components from the olefin oxidation reaction mass is of paramount economic concern, requiring recovery of substantially all of the precious metal catalyst components. This factor makes it economically advantageous to recover these catalyst metals in a physical state in which no additional processing is required to place them in condition for recycle to the oxidation reactor. Separate catalyst recovery and reactivation steps can introduce the risk of further catalyst losses.

When the desired ketone is sufficiently volatile, it may be separated from the crude olefin oxidation reaction mass by flashing. However, ketone recovered by this flashing technique will still be wet, containing water that flashes over along with the desired ketone. When the desired ketone is less volatile than water, the ketone must be recovered from the crude oxidation reaction mass by means other than flashing. Even if the ketone forms a second liquid phase in the crude reaction mass, there will be much ketone left in the aqueous phase. Thus, adequate recovery of ketone from the aqueous phase is a requirement of any economic process.

In designing process equipment for obtaining ketones from olefins, it is also convenient and economically favorable for the process equipment to be adaptable to a variety of ketone and/or aldehyde products and catalyst systems.

The present invention provides a method by which substantially all of the aldehydes are removed from a dry crude ketone-rich stream by use of the Tischtschenko condensation reaction. The present invention also provides a method for obtaining a dry crude ketone-rich substrate suitable for the removal of aldehydic impurities via Tischtschenko condensation. The present invention provides an integrated olefin-to-ketone process which satisfies the aforementioned process economic concerns. In one embodiment of the present invention, an extraction step, which when coupled with thermal distillations to make pure ketone product, creates a dry substrate suitable for treatment by Tischtschenko condensation. This extraction step also serves to separate the precious metal oxidation catalyst from the desired ketone products and oxidation byproducts without detrimental loss of precious metal catalyst components.

According to the present invention, aldehydes are removed from aldehyde-containing ketone mixtures by Tischtschenko condensation of the aldehyde into an ester, followed by overhead distillation of the ketone. An extraction step provides substantially dry, crude ketone to the Tischtschenko condensation step. In the extraction, the desired ketone product and oxidation byproducts are extracted to form an organic extractant phase while the precious metal catalyst remains in a second, aqueous raffinate phase suitable for recycle to the olefin and/or catalyst oxidation step without further treatment. Moreover, the extraction step advantageously creates a substantially dry ketone-rich stream, thereby eliminating the need to "break" any ketone-water azeotrope in order to obtain essentially dry pure ketone product. Subsequent distillations to recover the extraction solvent for recycle and to reject other non-aldehydic impurities from the desired ketone product will easily create the substantially dry ketone-rich stream suitable for Tischtschenko condensation of the aldehyde.

If the desired ketone product is suitably more volatile than water so that it can be economically recovered from the ketone crude by distillation, the extraction step can be advantageously applied to the flash-recovered wet crude ketone stream. This procedure, in combination with the normal distillations required for solvent and product recovery, will provide the substantially dry ketone-rich stream for subsequent treatment by Tischtschenko condensation.

Therefore, it is an object of this invention to provide a method to efficiently separate desired ketone products from their related aldehydic analogs by Tischtschenko condensation, without regard to the source of the aldehyde-containing ketone stream.

It is a further object of this invention to provide a substantially dry ketone-rich stream for contact with a Tischtschenko catalyst system to thereby condense aldehydic byproducts into higher boiling ester products, more easily separated from the desired ketone products by thermal distillation than the aldehyde substrate.

It is a still further object of this invention to provide an economically efficient process for the manufacture and recovery of high purity ketone products made by aqueous phase olefin oxidation in the presence of precious metal catalysts.

It is another object of this invention to provide a means for recovering and recycling substantially all of the precious metal oxidation catalyst in an active, usable form without deleterious accumulation of oxidation byproducts in the oxidation catalyst recycle stream.

It is an object of this invention to utilize an extraction solvent which, when recycled in small amounts to the olefin oxidation reactor, in small amounts with the precious metal catalyst recycle stream, does not adversely affect the olefin oxidation reaction kinetics.

It is another object of this invention to provide a simple overall process scheme to separate substantially dry ketone products from the olefin oxidation reaction mass while avoiding the formation of undesirable azeotropic composition of water and ketones.

It is an object of this invention to utilize an extraction solvent which enhances the separation of the desired ketone product and olefin oxidation byproducts from the other components of the olefin oxidation reaction mass.

It is yet a further object of this invention to provide a ketone separation scheme which is easily adaptable to a variety of olefin-ketone pairs and precious metal catalyst systems.

These and further objects of the present invention will become apparent to those skilled in the art with reference to the figures and detailed description which follow.

SUMMARY OF THE INVENTION

The present invention provides a process for obtaining a substantially aldehyde-free ketone product, without regard to the source of the ketone crude. In this process, a crude ketone stream containing a desired ketone product and an aldehyde contaminant is contacted with a Tischtschenko catalyst selected from the group consisting of multivalent metal alkoxides of the form $[M(OR)_n]$, where M is a Group IIIA, Group IIB, or Group IVB metal, R an alkyl group and n the valence state of metal M. Optionally, a chloride promoter is provided of the form $M'Cl_m$, where M' is Group II or Group IIIA metal and m the valence state of metal M'. The aldehyde components are condensed into ester products whose boiling points are substantially different than that of the desired ketone. These esters may then be easily separated by conventional thermal distillation.

The present invention further provides a process for obtaining a dry crude ketone stream, suitable for subsequent treatment by Tischtschenko condensation. Such a dry stream is necessary, because the Tischtschenko catalyst activity is adversely affected by water.

The present invention also provides an integrated process for obtaining high purity ketone products from aqueous phase catalyzed olefin oxidation. An olefin feed stream, and an aqueous phase catalyst stream, are provided to an oxidation reactor. In the one-stage reactor scheme, the olefin feed stream is combined with said catalyst phase in the presence of oxygen, to thereby obtain a ketone crude. The ketone crude contains desired ketone products, oxidation byproducts, and unreacted olefin feed components, all dissolved in, or mixed with the aqueous catalyst phase. Next, this ketone crude stream is contacted with an extraction solvent to form two liquid phases: a first substantially catalyst-free organic extractant phase which contains the desired ketone products, oxidation byproducts and the extraction solvent and a second, catalyst-containing aqueous raffinate phase. The aqueous raffinate phase is directly recycled to said olefin oxidation reactor. The organic extraction solvent is then recovered from said organic extractant phase and thereafter recycled to the extraction-contacting step. Substantially pure, anhydrous ketone product is recovered from the organic extractant phase by thermal distillation. The exact configuration of the thermal distillation of the extractant phase depends upon the relative boiling points of the extraction solvent and the desired ketone product. An anhydrous ketone-rich stream product is contacted with a Tischtschenko catalyst, to condense aldehydic impurities in the anhydrous ketone-rich stream product into ester products of boiling points different than the desired ketone. Thereafter the Tischtschenko catalyst, optional promoter, and ester products are separated from the anhydrous ketone-rich stream products to obtain a high purity ketone product.

Alternatively, if a Wacker-type olefin oxidation process is used, the recovered ketone-free catalyst system from the extraction step, now partially or totally in a reduced state, is reoxidized with an oxygen-containing gas before being recycled to the olefin oxidation reactor.

In certain preferred embodiments of the present invention, the ketone crude is depressurized (or flashed) after the olefin oxidation reaction to remove volatile and unreacted olefin feed components from the ketone crude. In other embodiments, this crude depressurization step may also be used to recover the desired ketone, and optionally the co-produced impurities, by causing these components to flash into a vapor stream which is then condensed into a liquid phase which is then subjected to extraction. Alternatively, or additionally, the ketone recovery may be enhanced by distillation of the ketone crude. Subsequent to the extraction-contacting step and the formation of the first organic extractant phase, at a point in the process scheme which is a function of the relative boiling points of the desired ketone product and the extraction solvent, a dry ketone-rich stream containing aldehydic impurities is subjected to Tischtschenko condensation to form higher boiling esters of these aldehydes, which are thereafter more easily separated from the desired ketone products by thermal distillation.

In one very specific embodiment of the process, the olefin feed stream is butene, the desired ketone product is methyl ethyl ketone and the extraction solvent is butane.

DETAILED DESCRIPTION OF THE INVENTION

Figure 1:
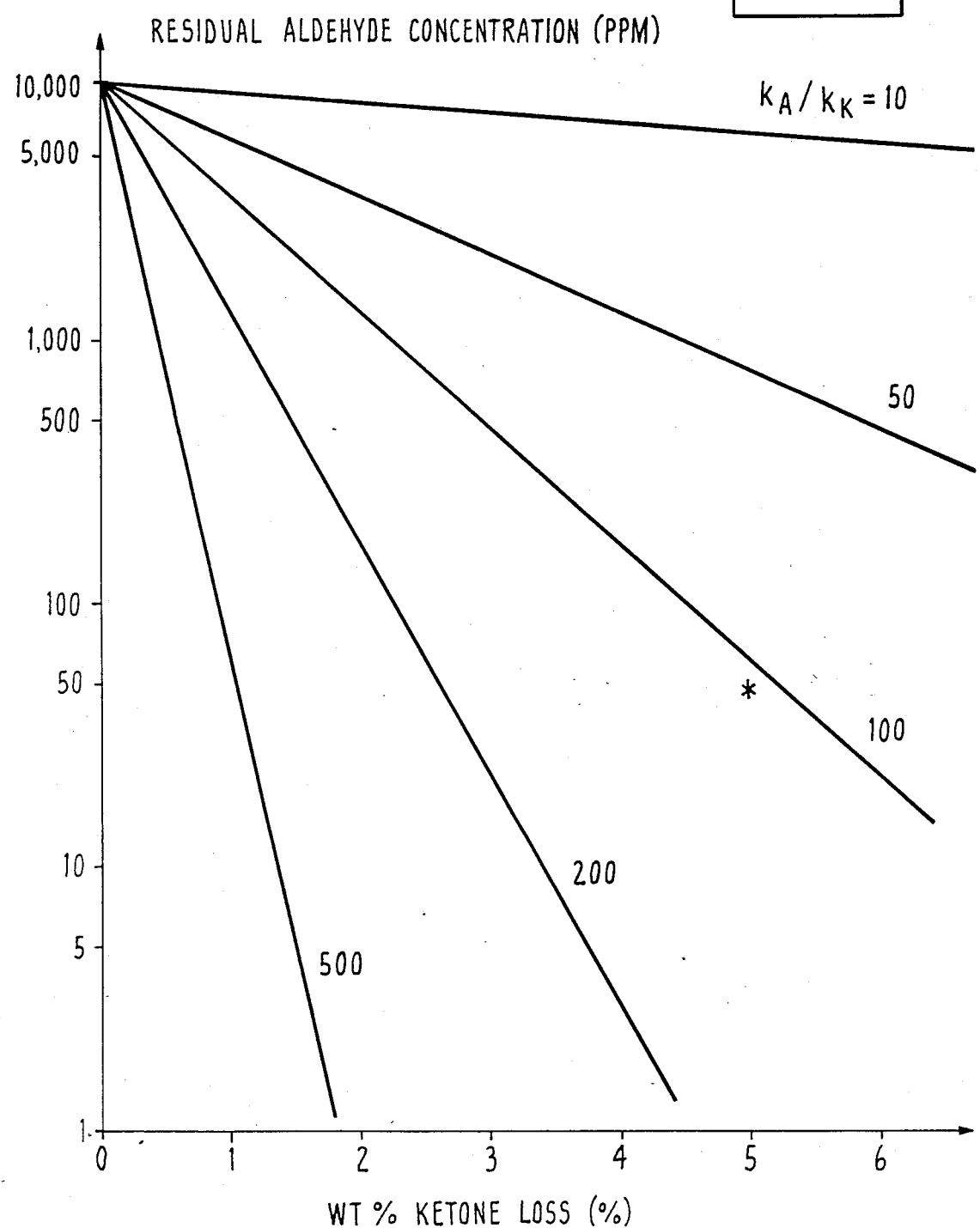
FIG. 1 is a graph which shows the ratio of the first order reaction rate coefficients for both the aldehyde and ketone in a batch or plug flow reactor to achieve a desired residual aldehyde concentration at specified ketone loss.

While the following description of the preferred embodiments of the invention focuses upon the separation of ketones from olefin oxidation reaction masses and the subsequent drying and treatment by Tischtschenko condensation for removal of aldehydic impurities, it will be appreciated by those skilled in the art that the invention is applicable to ketone products, generally, as obtained from aqueous phase catalyzed hydrocarbon oxidation. Further, the Tischtschenko condensation of aldehydic impurities can be generalized to aldehyde-containing ketone streams, however generated, for example by direct oxidation of alkanes.

Olefin oxidation processes have been developed to convert olefins to ketones in the presence of palladium and free oxygen. Typically, a water soluble palladium catalyst is introduced in the aqueous phase to insure generation of palladium cations. In the following descriptions, processes based upon co-feeding oxygen to the olefin oxidation reactor are described. It will be understood, however, that processes such as the Wacker process, in which the palladium catalyst solution is reoxidized in a separate reactor, are equally well suited to the present invention. Differences between the olefin oxidation processes, which are important for other reasons, aside, a common characteristic of all systems of this type is the accumulation of the desired ketone product in the aqueous, catalyst-containing phase, along with other olefin oxidation byproducts. High concentrations of the desired ketone in the aqueous phase can also lead to the formation of a ketone-rich organic phase. It is further recognized that certain processes, e.g., Murtha U.S. Pat. No. 4,507,507, include the addition of an organic diluent to improve olefin oxidation process kinetics. Mindful of all these variations in the olefin oxidation process scheme, it remains a common characteristic that the palladium catalyst and at least a portion of the desired ketone product accumulate in the same aqueous phase. The catalyst and the desired ketone must be carefully, efficiently and completely separated from each other in order to obtain a catalyst stream for recycle to the oxidation reactor and a substantially pure, anhydrous ketone product.

According to one embodiment of the present invention, the ketone crude, which hereinafter refers to the olefin oxidation reactor effluent stream, can comprise two liquid phases. The first phase is an aqueous phase comprising wholly or partially soluble palladium catalyst and co-catalyst components, the desired ketone product, oxidation byproducts, dissolved unreacted olefin components, and optional pH controlling components, including, but not limited to sulfuric acid. As noted above, if the concentration of ketone in this ketone crude exceeds its aqueous solubility, a second organic phase rich in ketone will form in equilibrium with the aqueous phase. This second organic phase, for purposes of the present invention, is subsumed within the definition of ketone crude as used hereinafter.

It is intended that processes employing aqueous phase catalyst systems other than palladium, useful in olefin oxidation to ketone products, are within the scope of the instant invention. Regardless of the specific precious metal catalyst used, the same overriding economic constraints govern process design, as efficient and complete precious metal catalyst recovery is a precondition to any economical process.

In investigating the separation of the precious metal catalyst from the desired ketone product, it was found experimentally that the presence of unreacted olefin feed components in the ketone crude led to palladium complexation which hindered the complete separation of the precious metal catalyst from the organic components. Since process economics requires quantitative recovery of the palladium from the ketone crude, palladium complex formation, having even slight solubility in an organic extraction solvent, must be avoided. According to the instant invention, one method of avoiding complex formation takes advantage of the fact that the vapor pressure of olefin feed components is typically higher than the vapor pressure of water and ketone products. This vapor pressure difference makes it possible to simply depressurize (or, flash) the ketone crude to remove unreacted olefin feed components. This flashing causes decomposition of the palladium-olefin complexes which may have formed in the olefin oxidation step or immediately subsequent to the oxidation step.

According to this invention, another related method for eliminating precious metal complexation and for improving precious metal catalyst recovery, is to react the remaining olefin feed components virtually to extinction in a post-olefin-oxidation reaction step. While this precious metal catalyst complex formation phenomenon is described here with reference to palladium, it is predicted that, for example, rhodium would also tend to form the same complexes with the unreacted olefin feed components.

Extraction

According to one aspect of the present invention, the ketone crude is contacted with an extraction solvent to obtain two liquid phases. In the first, an organic extractant phase contains the desired ketone products and the oxidation byproducts such as e.g. aldehydes. The second aqueous raffinate phase contains the water-soluble olefin oxidation catalyst which can thereafter be recycled to the olefin oxidation step. Any oxidation byproducts which could deleteriously accumulate in the aqueous raffinate phase, and thereby adversely affect olefin oxidation reaction kinetics are conveniently extracted into the extraction solvent where they can be more easily separated from the desired ketone product. The use of the extraction solvent to separate the desired ketone from the aqueous-soluble precious metal catalyst also results in the recovery of the desired ketone product in an organic phase that is substantially free of water, eliminating problems attendant to azeotrope formation, which is characteristic of many ketone-water mixtures.

The extraction solvent must be carefully selected with the following considerations in mind. The solvent must not form complexes with the olefin oxidation catalyst present in the ketone crude. The extraction solvent must also be capable of selectively extracting the desired ketone products, as well as the olefin oxidation reaction byproducts which would otherwise accumulate in the olefin oxidation catalyst recycle. The extraction solvent should be selected to eliminate the formation of any ketone-water azeotropes. The extraction solvent should also be chosen so as to be adaptable to a variety of olefin oxidation catalyst systems. Further, the extraction solvent should be chosen to simplify the separation of the extraction solvent from the desired ketone product, as both components must ultimately be obtained in substantially pure form, the ketone as product and the extraction solvent for recycle to the extraction step. The extraction solvent should be easily separated from all of the olefin oxidation reaction byproducts, preferably by simple thermal distillation. According to the present invention, the preferred class of solvents which addresses the above noted criteria is alkane compounds, including linear, branched and cyclic alkanes. Substituted alkanes, e.g., chloroalkanes, alcohols and others, can also be useful provided that these solvents meet the other criteria set forth above. Petroleum ether can also be used.

As noted above, part of the process of the instant invention involves depressurizing the ketone crude to remove unreacted olefin feed components which tend to complex with the precious metal olefin oxidation catalyst. For this same reason, the extraction solvent must be free of carbon-carbon double bonds, and substantially free of unsaturated impurities. A particularly preferred group of extraction solvents comprises butane, pentane, hexane, heptane, octane, nonane and decane. It is possible to select an extraction solvent which corresponds to the olefin substrate. The extraction solvent can then often be directly obtained in sufficient quantities from the olefin feed stream.

Since the relative boiling points of the desired ketone product and the extraction solvent are partially determinative of the particular details of the separation set 4 (see FIG. 3), according to the present invention, there are identified two classes of extraction solvents whose boiling points fall respectively below and above that of the desired ketone products and oxidation byproducts. Those extraction solvents boiling, below the ketone product, e.g., the butane-methyl ethyl ketone pair, will hereinafter be referred to as low-boiling extraction solvents. Conversely, an extraction solvent whose boiling point exceeds that of the desired ketone product is hereinafter referred to as a high-boiling extraction solvent. The terms low-boiling and high-boiling are "relative" and therefore descriptive of the desired ketone-extraction solvent pair and are not descriptive of the extraction solvent alone.

Tischtschenko Condensation

Another process design consideration encountered in separating the desired ketone product from the olefin oxidation reaction mass involves the separation of the desired ketone product from its aldehyde analog, unavoidably formed during olefin oxidation. The difficulty in separating the ketones and aldehydes derives from the molecular weight and boiling point similarities between a ketone and its aldehyde analog which makes thermal distillation an impractical method of separation. According to the present invention, after the extraction solvent contacting step, which provides the desired ketone product and undesired aldehydic impurities in the same substantially dry organic extractant phase, the solvent phase is distilled to remove the remaining water overhead along with other volatile impurities made in the oxidation reaction. If a volatile solvent has been used in the extraction step, it, too, is removed in this distillation step. The resulting anhydrous ketonealdehyde phase, with or without the extraction solvent, is subjected to Tischtschenko condensation to selectively condense the unwanted aldehydes into higher molecular weight ester products which can be much more easily separated by distillation from the desired ketone than can the simple aldehyde analog. Since the Tischtschenko reaction is extremely selective for aldehydes, ketones are unaffected. This enables separation of the unwanted aldehydic impurities without an uneconomic loss of the desired ketone product. This is in distinction to prior art such as aldol condensation methods as exemplified in U.S. Pat. No. 3,198,837; U.S. Pat. No. 3,392,200; Japanese Pat. No. J56-158725; U.S. Pat. No. 4,329,510; and Japanese Pat. No. J58-208246. These methods of providing ketone products substantially free of aldehydic impurities suffer from consumption of the desired ketone product due to the non-specificity, and hence lower selectivity, of the aldol condensation reaction. Indeed, while it is known that ketones can undergo aldol condensation into an aldehyde-alcohol (or "aldol") product, ketones cannot undergo Tischtschenko condensation into an ester product, by virtue of the absence of alpha-hydrogen atoms on the carbonyl group of the ketone. This does not exclude the possibility, however, of reducing active ketones with aldehydes. For instance, Lin I. and Day A. R. ("A Study of Mixed Tischtschenko Reaction," J. Amer. Chem. Soc., 74, 5133, 1952) disclose that, while acetone and cyclohexanone do not undergo Tischtschenko condensation with butyraldehyde, 1,3-dichloroacetone does undergo so-called mixed Tischtschenko condensation. Therefore, the specificity of the Tischtschenko reaction for a given aldehyde/ketone pair, while being eventually anticipated but not necessarily expected, always requires experimental verification and demonstration.

In addition to differing in the nature of the condensation product that is being formed (i.e., aldol versus ester), aldol condensation also differs from Tischtschenko condensation in terms of the specific reaction conditions and catalyst systems that are used. For instance, whereas aldol condensation typically uses alkali or alkaline earth hydroxides or oxides at relatively elevated temperatures, Tischtschenko condensation typically requires multivalent metal alkoxides and is favored at lower temperatures. In addition, while aldol condensation is usually carried out in aqueous solution (water being, in addition, a byproduct of the condensation reaction), the activity of Tischtschenko catalysts is said to be adversely affected by small amounts of water (see, for instance, W. C. Child and H. Adkins, "The Condensation of Aldehydes to Ester By Aluminum Ethoxide," J. Amer. Chem. Soc., 45, 301. December, 1923). It is theorized that water hydrolyzes part of the Tischtschenko alkoxide catalyst into hydroxyl derivatives. Similar deactivation effects have also been reported for alcohols.

According to the Tischtschenko reaction as applied in the present invention, multivalent, including trivalent (Al III) or tetravalent (Ti IV), metal alkoxides are used to catalyze the aldehyde condensation in the liquid phase. The catalysts useful in the Tischtschenko reaction are variously described in the literature. For example, see W. C. Child and H. Adkins, "The Condensation of Aldehydes to Ester By Aluminum Ethoxide," J. Amer. Chem. Soc., 45, 3013 (December, 1923); W. C. Child and H. Adkins, "The Condensation of Aldehydes to Ester by Alkoxides," J. Amer. Chem. Soc., 47, 798 (March, 925); M. S. Kulpinsky and F. F. Nord, "Essential Steps in the Catalytic Condensation of Aldehydes: New Synthesis of Glycol Esters," J. Org. Chem., 8, 256-70 (1943); Van Schaak U.S. Pat. No. 1,700,103; F. J. Villani and F. F. Nord, "Glycol Esters from Aldehydes," J. Amer. Chem. Soc., 68, 1674 (1946); Lin, I. and Day, A. R., "A Study of Mixed Tischtschenko Reaction," J. Amer. Chem. Soc., 74, 5133 (1952). The relevant portions of these references are hereby incorporated by this reference. Here, the metal alkoxides are generally represented by the formula $[M(OR)_n]$, where M is a Group IIIA, Group IIB, or Group IVB metal, R an alkyl group and n the valence state of metal M. Particularly preferred catalysts include aluminum isopropoxides, aluminum butoxides, aluminum ethoxide and titanium ethoxide. However, any catalyst that is useful for Tischtschenko condensation of aldehydes can be applied within the frame of the present invention.

In addition, Tischtschenko catalysts can optionally be used in combination with a chloride promoter of the form $M'Cl_m$, wherein M' is Group II or Group IIIA metal and m is equal to the valence state of metal M'. Preferred promoters include $ZnCl_2$, $HgCl_2$, $CaCl_2$ and $AlCl_3$. While the true function of the chloride promotor is not known, it is believed that its promoting effect is due, at least in part, to the scavenging of contaminant water molecules. Hence, any promotor that is also a water scavenger, would be expected to have a beneficial effect on the condensation reaction.

It is essential to note that water is known to deactivate the Tischtschenko catalysts. It is theorized that water causes the formation of a surface metal hydroxide which diminishes the catalyst activity. While it is not known how much water can be tolerated in the feedstock, our experiments described in the examples below show that it is crucial to have an essentially dry ketone-/aldehyde feedstock. We have found that the processes described herein, comprising extraction and thermal distillation, are very effective in insuring that the ketone substrate, containing aldehydic impurities, for the Tischtschenko condensation reaction is substantially dry.

Organic acids are theorized to have a similar deactivating effect on Tischtschenko catalysts. Therefore, if the crude ketone stream contains organic acids, their removal by scrubbing with an alkaline solution or by distillation or by some other means is recommended. Likewise, as alcohols have also been reported to deactivate Tischtschenko-type catalysts, it is important to minimize the alcohol concentration in the feedstock.

The amounts of catalyst and promotor required depend on the particular feedstock composition, but typically vary from 0.001 to 0.1 moles of alkoxide catalyst per mole of aldehyde in the feedstock, and 0.00001 to 0.1 moles of promotor per mole of aldehyde in the feedstock, respectively.

Figure 2:
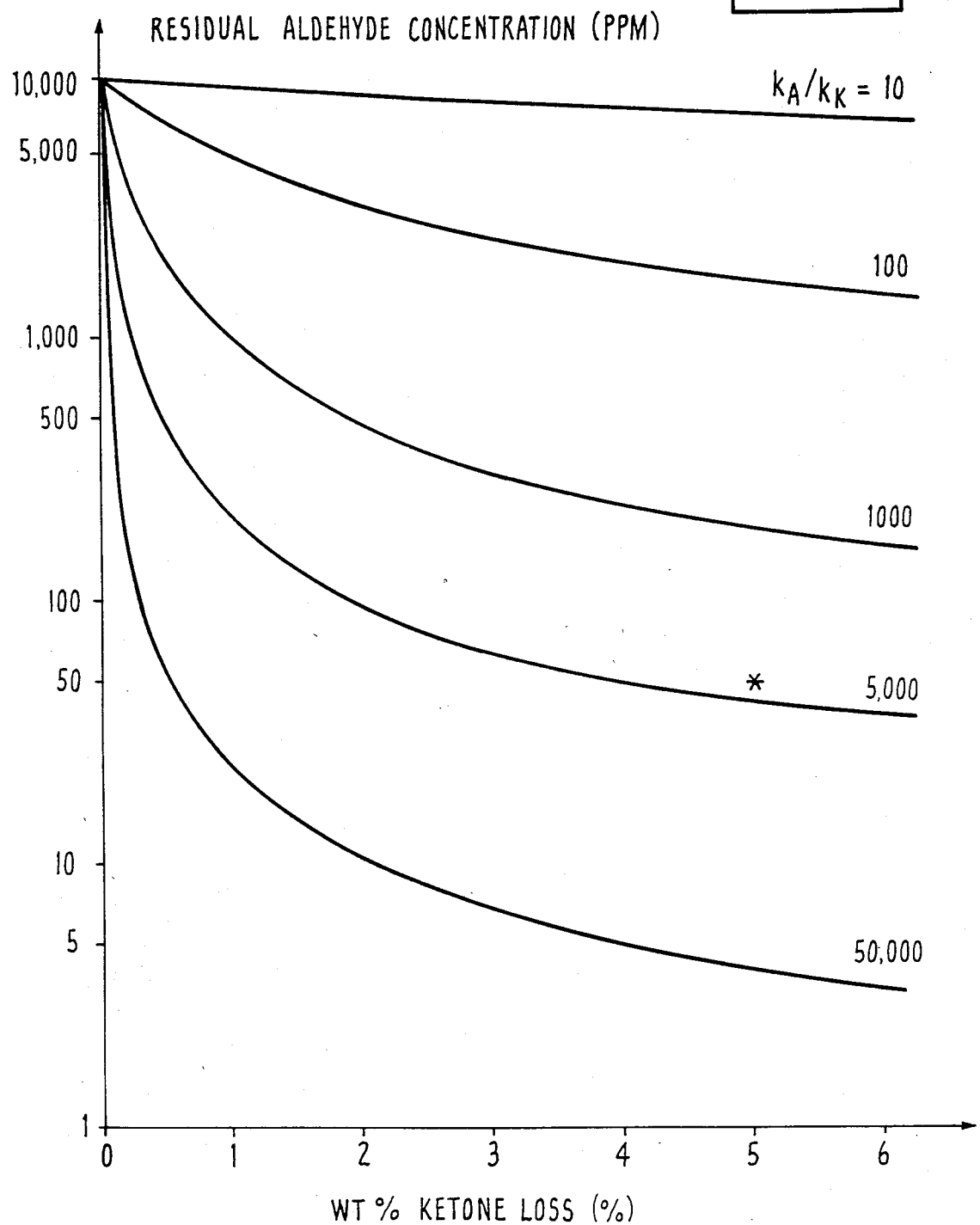
FIG. 2 is a graph which shows the ratio of the first order reaction rate coefficients for both the aldehyde and ketone in a backmixed reactor to achieve a desired residual aldehyde concentration at specified ketone loss.

Both liquid state (e.g., aluminum secondary butoxide) or solid state (e.g., aluminum isopropoxide) catalysts can be used in the condensation operation. The condensation reaction can therefore be carried out in an all-liquid or liquid/solid mode of operation. FIGS. 1 and 2, which have been, described above, additionally suggest that a batch or plug flow operation is preferred.

In some instances it may be advantageous to dissolve the Tischtschenko condensation catalyst in an organic solvent for convenient addition to the substantially pure, dry ketone stream. Moreover, the Tischtschenko condensation reaction can be conducted in an added solvent, which, for practical reasons, should be the same solvent as used to dissolve the Tischtschenko catalyst. The solvent must be chosen mindful of the need to subsequently separate the Tischtschenko reaction solvent from the desired ketone product. Some organic solvents which meet this design criterion are carbontetrachloride, heptane, xylene, petroleum ether, benzene and chloroform.

Preferred conditions for the Tischtschenko condensation are substantially the same as those that have been reported in the referenced literature. Optimum conditions are, however, a unique function of the particular aldehyde/ketone feedstock that needs to be treated, and will, therefore, have to be determined for each specific case. While it is the intent to apply the reaction to reduce aldehyde concentrations from several weight percentages in the ketone feedstock mass down to parts per million concentration levels, there is no upper limit to the aldehyde concentration in the feedstock other than set by the fact that the ketone is the desired product.

The Tischtschenko reaction is preferably conducted between 0° C. and 100° C., more preferably between 20° C. and 70° C. The optimum temperature will, however, have to be determined for each specific feedstock and catalyst/promotor system.

In particularly preferred embodiments of the subject invention, in the production of methyl ethyl ketone from butene, the undesired aldehydic impurity is butyraldehyde which is the aldehydic analog of methyl ethyl ketone. Butyraldehyde is condensed to butyl butyrate upon Tischtschenko condensation.

Figure 3:
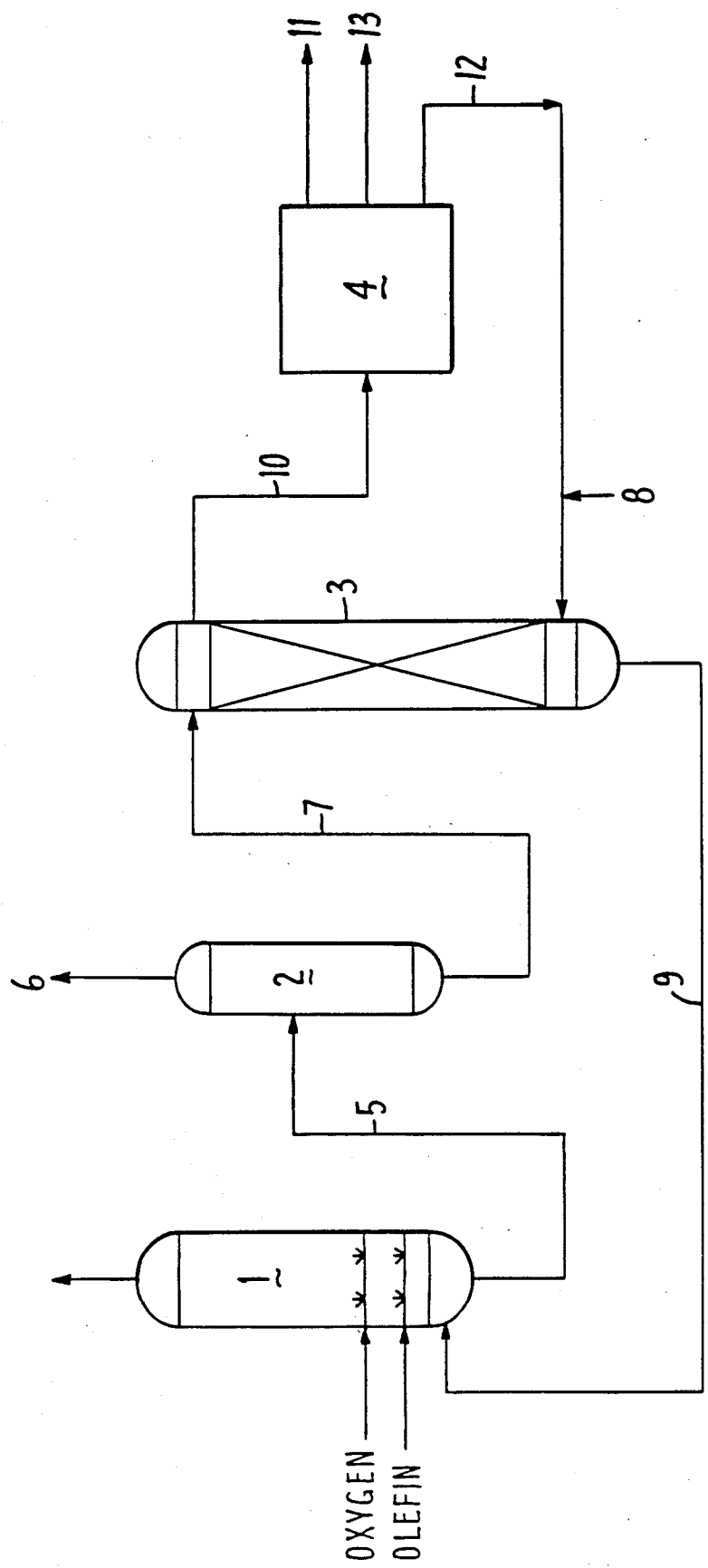
FIG. 3 is a flow diagram describing a generalized process according to the present invention.

Referring now to the process schematic shown in FIG. 3, a generalized flow diagram of the integrated process according to the present invention is presented. All of the flow diagrams and process descriptions are based on completely water soluble precious metal oxidation catalysts systems. These flow diagrams are presented to illustrate the preferred embodiments and are not intended to limit the scope of the present invention. In the case that the olefin oxidation catalyst is only partially dissolved, the process design may include a solid-liquid separation means, e.g., a centrifuge or filter plus a means for returning the solid catalyst mass to the olefin oxidation reactor. As seen in FIG. 3, the major process components include an olefin oxidation reactor 1, a flash separator 2, a contactor 3 and a separation set 4. Of these components, separation set 4 is generically represented in this figure since the order of the separation scheme is dependent upon the boiling points of the extraction solvent and the desired ketone product relative to each other. The olefin oxidation reaction which occurs in oxidation reactor 1, and the depressurization of the ketone crude 5 in the flash separator 2 to obtain unreacted olefin components 6 and a flashed ketone crude 7, have been previously described. According to this embodiment of the present invention, the depressured ketone crude 7 is next fed countercurrent to an extraction solvent stream 12 in a multistage contactor 3. An extraction solvent make up stream 8 is provided as necessary. The extract 10 is a substantially water-free organic phase which comprises the extraction solvent, the desired ketone products, and oxidation reaction byproducts. The specific characteristics of the extraction solvent are more fully described below.

The raffinate is an aqueous phase containing the precious metal oxidation catalyst which is recycled to the olefin oxidation reactor 1 through catalyst recycle stream 9. As a result of the extraction solvent contacting step, the raffinate phase is substantially reduced in its content of oxidation byproducts which could deleteriously accumulate in the olefin oxidation reactor 1, and thereby reduce olefin oxidation reaction rates and selectivities to the desired ketone products.

The organic extractant phase 10 is then further separated to obtain a substantially pure, anhydrous ketone product 11, the organic extraction solvent 12 for recycle to contactor 3, and a waste stream 13 containing unwanted oxidation byproducts. The details of separation set 4 are more fully described below with reference to FIGS. 4 and 5.

One step of the instant invention, which is included in separation step 4 but is not specifically illustrated in the generalized process flow diagram of FIG. 3, is the Tischtschenko condensation of the aldehydic impurities contained in the organic extractant phase 10 from the contactor 3. Since organic extractant phase 10 is bound to contain some residual water, it is not advisable to subject organic extractant phase 10 to the Tischtschenko reaction without first rendering the ketone-containing stream substantially anhydrous by distillation. The configuration of separation step 4 to generate a substantially anhydrous ketone-containing stream is a function of the boiling point relationship between the extraction solvent and the desired ketone product. Once the boiling point relationship is fixed, it then becomes possible to determine the proper placement of the Tischtschenko reaction in the overall process scheme of separation step 4 to thereby remove undesirable aldehydic impurities. In the event that separation set 4 produces substantially pure, anhydrous ketone product 11 which has not been previously treated to remove aldehydic impurities, the Tischtschenko treatment may be effected downstream of separation set 4.

Before describing by way of illustration a preferred embodiment of the instant invention in which methyl ethyl ketone is obtained from butene, the present invention is intended to be applicable to catalytic olefin oxidation as that term is broadly used. Within the scope of this invention are intended to be such olefin oxidation substrates as any hydrocarbon containing at least one carbon-carbon double bond, or mixtures of such hydrocarbons. The olefinic hydrocarbon, which contains at least two carbon atoms per molecule, can be either substituted (e.g., 4-methyl, 1-pentene) or unsubstituted (e.g., 1-pentene), and either cyclic (e.g., cyclohexene) or acyclic (e.g., 2-hexene). If the olefinic hydrocarbon is acyclic, the carbon-carbon double bond can be either terminal (so-called alpha-olefins) or non-terminal (so-called internal olefins). If the olefinic hydrocarbon contains more than one carbon-carbon double bond, the double bonds can be conjugated or unconjugated. No particular upper limit applies to the carbon number of the olefinic hydrocarbon. However, a practical limitation for the oxidation reaction is that both the reactivity of the hydrocarbon and selectivity to the ketone compound(s), as a rule, tend to decrease with increasing carbon number.

Specific reaction conditions and catalyst compositions for olefin oxidation are set forth, for example, in a description of the Wacker process which appears in Chemical Engineering News, Volume 50, July 8, 1963, and in reduced chloride systems described, e.g., in U.S. Pat. No. 4,507,507. Other olefin oxidation reaction catalysts and conditions which are relevant to the preferred embodiment described below can also be found in our U.S. Pat. No. 4,720,474 and U.S. Pat. No. 4,723,041. The relevant portions of both patents are hereby incorporated by this reference.

Figure 4:
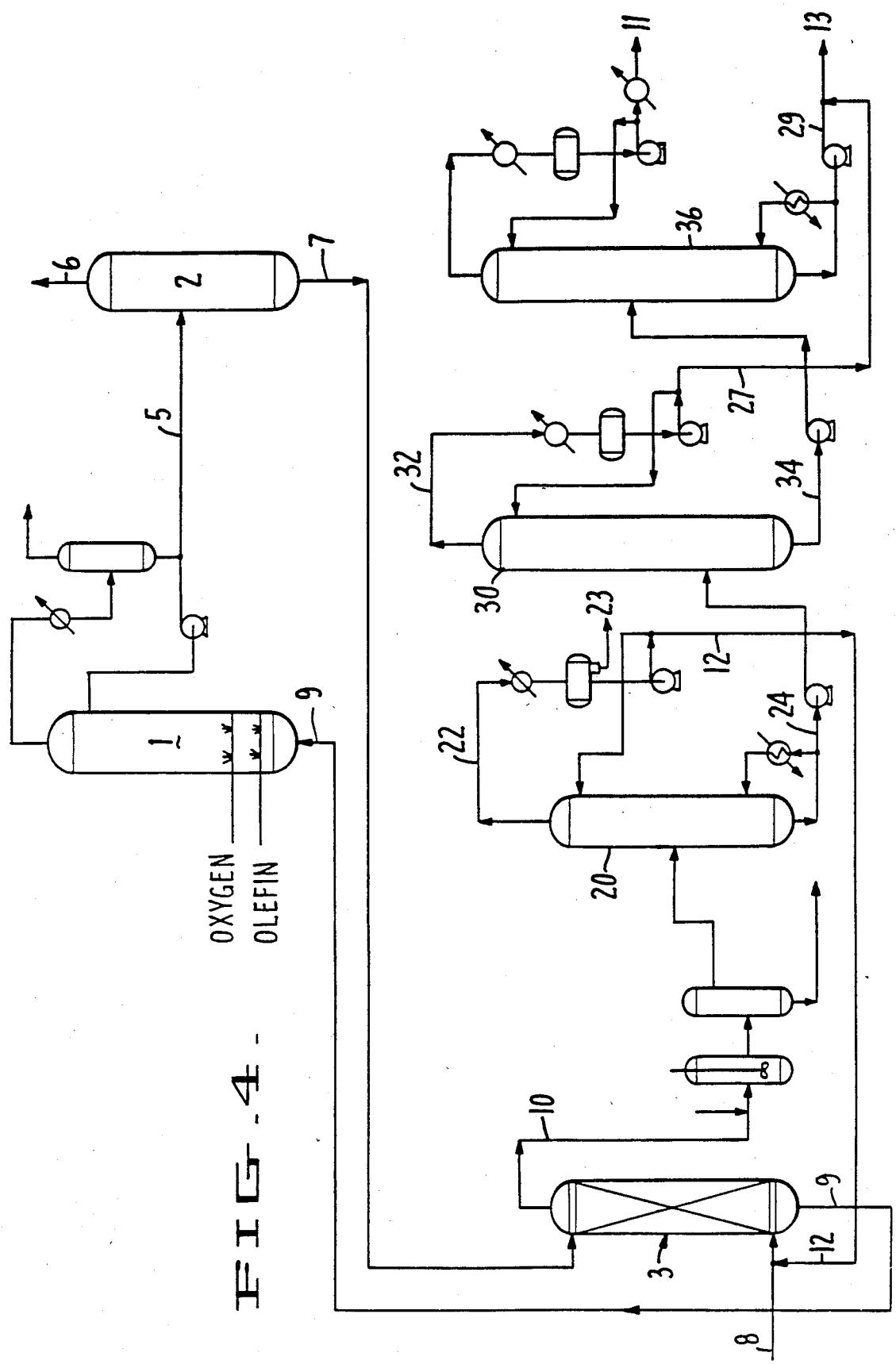
FIG. 4 is a process flow diagram which shows the process equipment used to obtain ketone products from olefins wherein oxygen is co-fed to the olefin oxidation reactor and wherein an extraction solvent is used which has a boiling point lower than the desired ketone.
Figure 5:
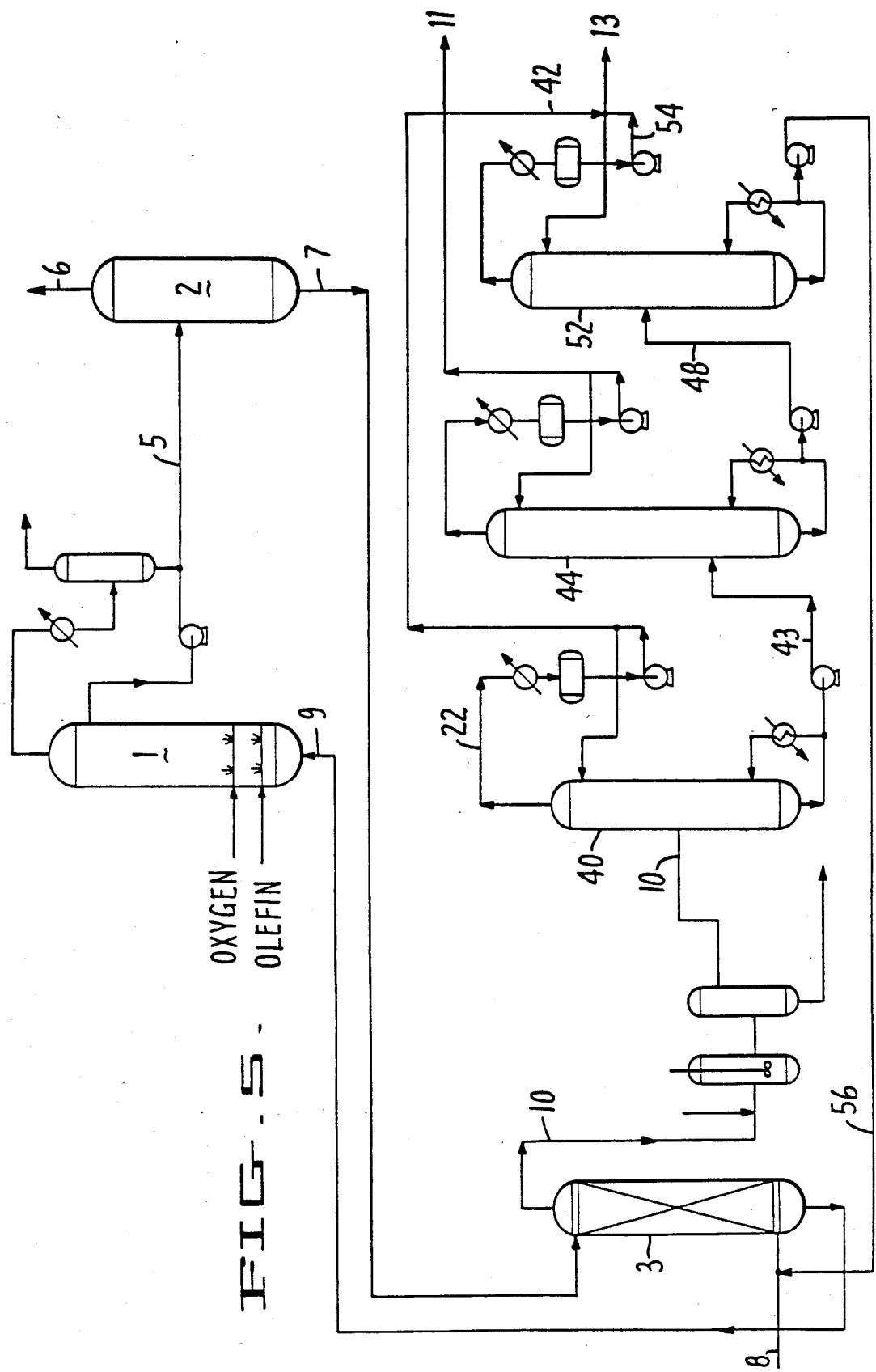
FIG. 5 is a process flow diagram which shows modifications to the process schematic shown in FIG. 4 when an extraction solvent is used which has a boiling point higher than the desired ketone product.

For clarity, and to avoid duplication, the same numerals will be used throughout the following descriptions of FIGS. 3 through 5 to refer to equivalent process components and process streams. A detailed description shall be given only once with the intention to incorporate that detail, when necessary, in the subsequent description.

Referring specifically to FIG. 4, a preferred embodiment of the process is shown. In this preferred embodiment, the olefin feed stream is a mixed butene stream, the desired ketone product is methyl ethyl ketone ("MEK") and the extraction solvent is chosen to be butane. Although this description is made with reference to this specific embodiment, it will be recognized by those skilled in the art that this process scheme is applicable to a wide range of combinations of olefin feed, desired ketone, and extraction solvent systems in which the extraction solvent has a boiling point lower than the desired ketone product and oxidation byproducts. This is in contrast to the process scheme set forth below with reference to FIG. 5 in which the extraction solvent has a boiling point higher than the boiling point of the desired ketone product.

Low-Boiling Extraction Solvent

A process flow scheme in which the extraction solvent has a boiling point lower than the boiling point of the desired ketone product, as for example in the butene-MEK-butane system, is shown in FIG. 4. The crude ketone 7, which has been depressurized to remove unreacted olefin feed components, is fed to a contactor column where it is passed countercurrent to the extraction solvent 12 which is fed to the bottom of the contactor column 3. Make up extraction solvent 8 is added as needed. The denser, aqueous raffinate phase 9, containing the oxidation catalyst, is withdrawn from the bottom of the column 3; the lighter, organic extractant phase 10 is taken overhead. Using, for example, a mixer-setter pair as illustrated, the organic extractant phase 10 is subsequently neutralized to reduce residual organic acid byproduct acidity to obtain an organic extractant stream which is not corrosive to the downstream process equipment, enabling the use of carbon steel as a material of construction. Removal of the organic acids also assures that their presence will not interfere with the subsequent treatment with Tischtschenko catalyst.

In designing the contactor column 3, any number of liquid-liquid contact media, e.g., saddles, rings, etc., or mechanical means can be chosen to facilitate two liquid phase contact and component separation. The number of theoretical stages which are required to effect the necessary separation of the desired ketone from the aqueous phase is a function of many parameters including the extraction solvent selection, the flashed ketone crude 7 composition, the temperature of the various feed streams, and the extraction solvent/crude ketone feed ratio. Optionally, a series of mixers and settlers may be used instead of contactor column 3. Liquid-liquid extraction is a common unit operation. Choosing precise design and operating criteria such as the type of contactor best suited for the application, feed locations and volume rates is within the capability of one skilled in this art. Additional information related to liquid-liquid extraction design may be found, e.g., in W. L. McCabe and J. C. Smith, Unit Operations of Chemical Engineering, Chapter 20 (McGraw-Hill, 1976); R. Treybal, Liquid Extraction, 2nd Ed. (McGraw-Hill, 1963); R. H. Perry and C. H. Chilton, Chemical Engineers' Handbook, 5th Ed., Section 21 (McGraw-Hill, 1973). See the working examples below for specific data on the butane, methyl ethyl ketone and water system, including the ternary composition diagram shown in FIG. 6, for further information useful in the present invention.

In the specific embodiment for producing methyl ethyl ketone from butene described herein, it is anticipated that from three to seven theoretical stages would be required to efficiently separate methyl ethyl ketone from the aqueous catalyst-containing ketone crude.

It is in the next process step that the relationship between the extraction solvent boiling point and the desired ketone product boiling point becomes important. In the case of FIG. 4, the extraction solvent has a boiling point below that of the desired ketone product and byproducts so that the extraction solvent plus essentially all of the water remaining in the extract phase are taken overhead (as stream 22) from a solvent stripping column 20. The organic phase formed by the condensation of overhead stream 22 is partly used as reflux to the solvent stripping column 20 and is also recycled to the contactor column 3 through stream 12. An aqueous phase 23 which may form in the separator drum by condensation of stream 22 is discarded.

The stripping column bottom product 24 is then distilled in a light ends column 30 to reject low boiling impurities 32 made in the olefin oxidation step. This light ends distillation provides further assurance that any trace water in stream 24, perhaps as the result of a temporary upset in solvent stripping column 20, will be rejected overhead to yield an anhydrous ketone product 34 as the bottoms of this thermal distillation. Stream 34 is treated in condensation reactor 33 to remove aldehydic impurities by use of the Tischtschenko condensation reaction described above, to form higher boiling ester products which are more easily separated from the desired ketone product than the aldehyde analog.

After the Tischtschenko condensation reaction, the treated ketone bottoms product 34 is distilled in ketone column 36 to obtain high purity ketone product overhead 11 and heavy ends 29. If they are soluble and were not removed prior to distillation in ketone column 36, the Tischtschenko catalyst and promoters or their residues will be part of heavy ends stream 29. Stream 29 is joined with the non-aqueous low boiling impurities 27 to become organic waste stream 13 which is thereafter properly and safely disposed of, for example, by incineration.

The light ends column 30 and the ketone column 36 comprise standard thermal distillation apparatus. The design parameters for these distillation columns are a function of the feed stream composition, product capacity, final product specifications and the desired energy efficiency. Ideally, these columns will be useful in the production of several ketone products, from a variety of ketone crude compositions. The interchangeability of all of the process equipment may be a contributing factor to enhanced process economics. The ability to calculate the number of theoretical stages required in the thermal distillations, and the product through-put requirements is within the skill of an ordinary worker in this art.

High Boiling Extraction Solvent

In another embodiment of the present invention, the extraction solvent has a boiling point which is higher than the boiling point of desired ketone product. As a result of this relationship between boiling points of the desired ketone product and extraction solvent, a somewhat different process scheme must be utilized to separate the desired ketone from the extraction solvent. One specific embodiment, utilizing a high boiling extraction solvent to separate the desired ketone product from the aqueous catalyst phase is shown in FIG. 5. In describing the apparatus of FIG. 5, like numerals will be used to refer to like components and process streams as was described with reference to FIG. 4.

As in the case of low boiling solvents, depressurized ketone crude 7 is fed countercurrent to the extraction solvent 56 in the contactor 3. Make-up extraction solvent 8 is added as needed. The denser, aqueous raffinate phase 9, containing the oxidation catalyst, is withdrawn from the bottom of column 3. The lighter, organic extractant phase 10 is taken overhead. The organic extractant phase 10 is subsequently neutralized to reduce residual organic acid byproduct acidity to obtain an organic extractant stream which is not corrosive to the downstream process equipment, enabling the use of carbon steel as a material of construction. After the neutralization steps, the organic extractant phase 10 is fed to a light ends column 40 to take low boilers and water overhead in stream 42, which is eventually incinerated. The bottoms product 43 from column 40, contains the desired ketone product and the extraction solvent. Although not specifically shown in FIG. 5, the substantially anhydrous bottoms product 43 is treated via Tischtschenko condensation of the unwanted aldehydic impurities in condensation reactor 33. This treated stream 43 is then fed to a ketone column 44. The desired ketone product is taken overhead as stream 11. The higher boiling extraction solvent remains as bottom product stream 48 which is thereafter fed to a heavy ends column 52 in which substantially pure extraction solvent is taken as a bottoms product 56 and recycled to the contactor 3. If they have not been previously removed, Tischtschenko catalyst and promoter or their residues may be removed from this recycle solvent stream 56 by any conventional means. The heavy ends stream 54 is joined with light ends stream 42 to become waste stream 13, which may be sent to incineration.

EXAMPLES

EXAMPLE 1

Figure 6:
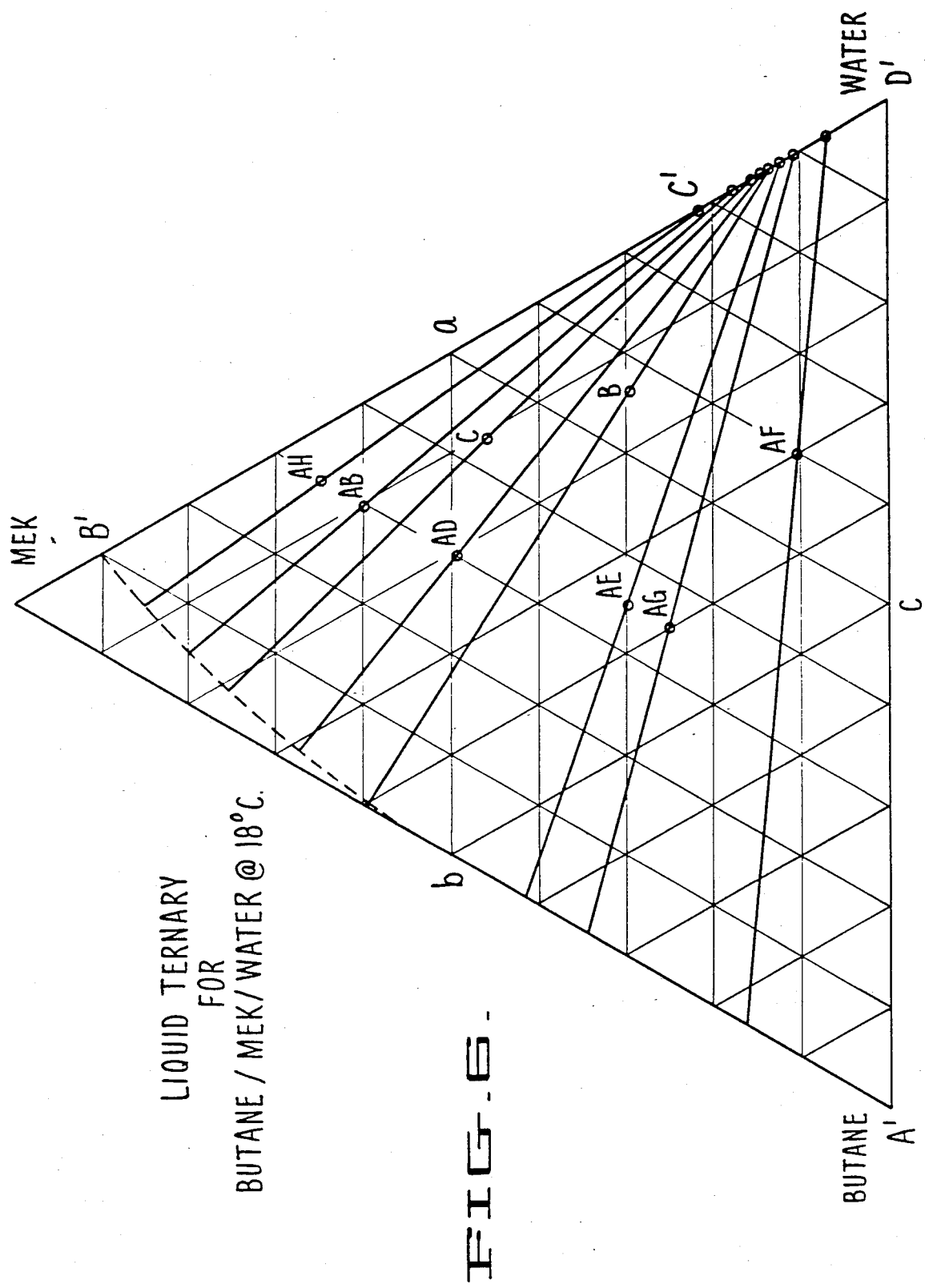
FIG. 6 is a ternary phase diagram for the butane, methyl ethyl ketone and water system at 18° C.

FIG. 6 shows a ternary diagram for the butane, methyl ethyl ketone and water system at 18° C. The binodal curve A'B' was determined by turbidity experiments. The tie lines were determined by making synthetic mixtures of butane, MEK and water whose compositions were known (e.g., mixture point AB). Thereafter, the phases were separated and the compositions of the water-rich layers were determined by gas chromatography. The pressure above the synthetic mixtures was kept sufficiently high to insure that essentially all of the butane remained in the liquid state. From the ternary diagram, it can be seen that butane is an efficient solvent for MEK.

EXAMPLE 2

Figure 7:
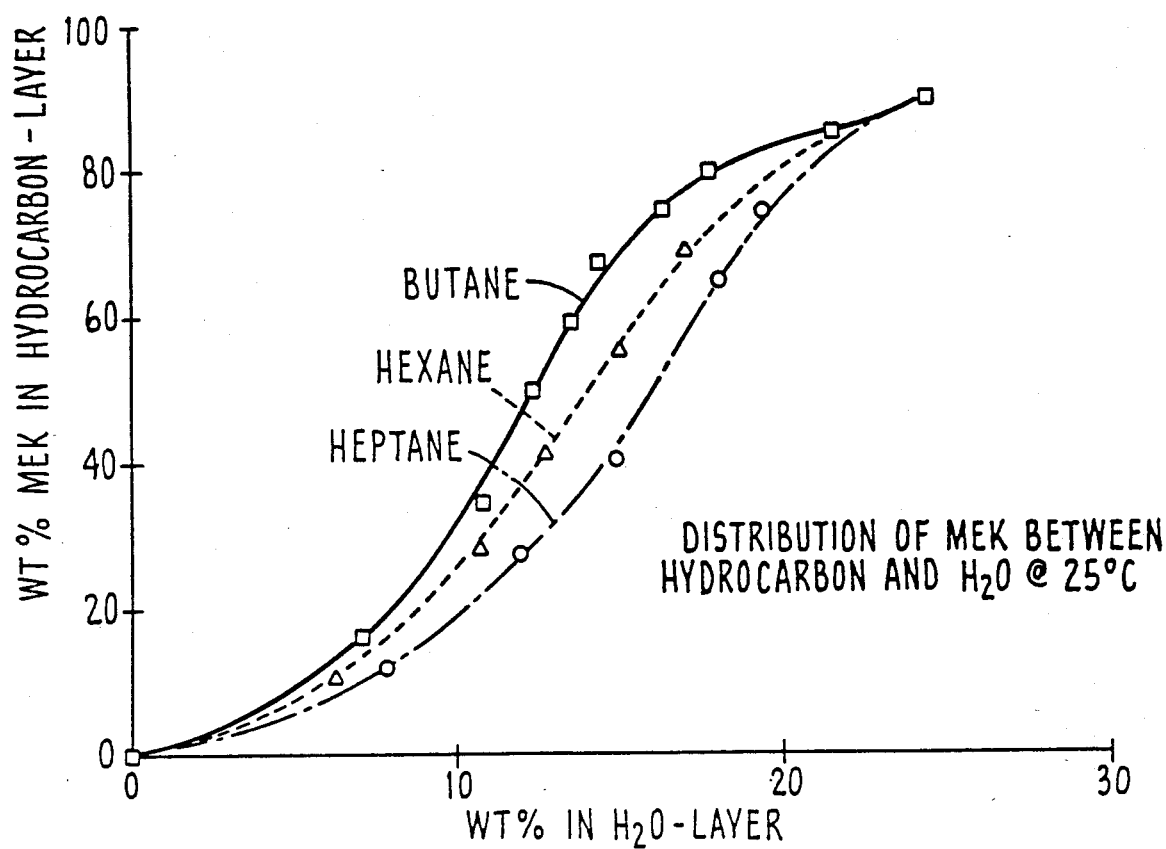
FIG. 7 illustrates equilibrium curves for butane from the ternary diagram of FIG. 6, and equilibrium curves for hexane and heptane as solvents at 25° C. obtained form the open literature, R. E. Treybal, O. J. Vondrak, Industrial & Chemical Engineering, Vol. 41, No. 8, pp. 1761–63 (August, 1949).

The ternary diagram shown in FIG. 6 was used to generate the equilibrium curve for butane shown in FIG. 7. The pairs of points obtained from the intersection of each tie line with the two binodal curves A'B' and C'D' in FIG. 6 were used to develop the butane equilibrium curve shown in FIG. 7. This equilibrium curve for butane, as well as the equilibrium curves for hexane and heptane at 25° C. obtained from work of R. E. Treybal, O. J. Vondrak, Industrial & Engineering Chemistry, Vol. 41, No. 8, pp. 1761-63, August, 1949, can be used to develop stage by stage composition calculations according to methods well known to those skilled in the art. From the data presented in FIG. 7, it is apparent that lower alkanes are more selective solvents for MEK than the higher alkanes.

EXAMPLE 3

Figure 8:
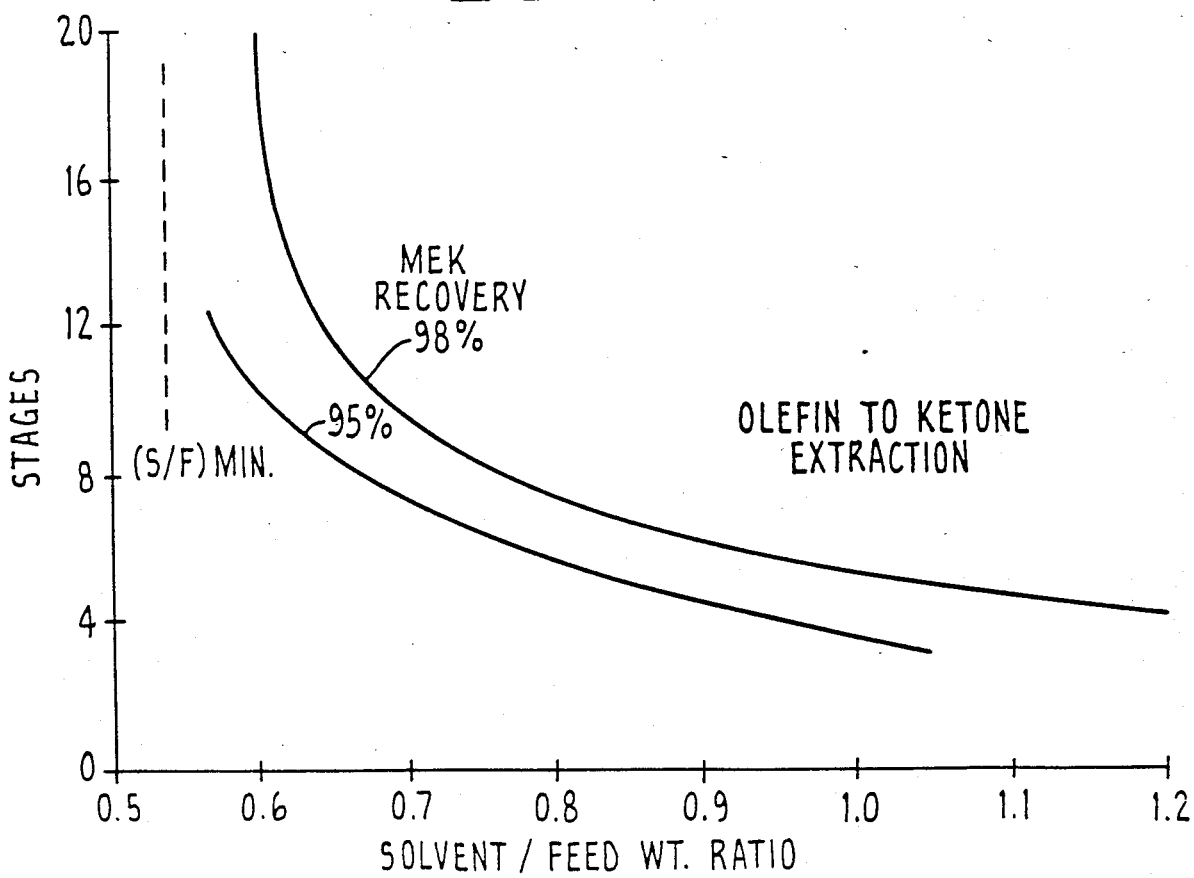
FIG. 8 illustrates the number of theoretical countercurrent stages required to recover methyl ethyl ketone from a water solution containing 15% methyl ethyl ketone, as a function of the butane to water feed ratio.

Based upon the information developed from the ternary diagram of FIG. 6 and the equilibrium curve for butane shown in FIG. 7, the number of theoretical stages required to recover MEK from an aqueous phase containing 15% MEK is plotted against the solvent to feed ratio (by weight) in FIG. 8.

EXAMPLE 4

A mixture as shown in Column I of Table 1 was prepared at room temperature in a well stirred vessel. After the stirring was stopped, and the phases were allowed to separate, the composition of each phase was measured by GC analysis. The recovery in each phase, reported in columns II and III, shows that 86.5% MEK is removed in this single stage operation. This data also indicates that butane appears to be an efficient solvent for removing the other non-ketone byproducts which one might expect to be present in olefin oxidation reaction masses.

TABLE 1

| | COMPOSITION (gms) | | | |
|---|---|---|---|---|
| Compound | Original Mixture I | Water-Rich Phase II | Butane-Rich Phase III | Recovery in Butane-Rich Phase, % |
| Water | 2.0807 | 1.9026 | 0.1781 | — |
| MEK | 3.3952 | 0.4569 | 2.9383 | 86.5 |
| Butane | 0.3153 | trace | 0.3153 | — |
| Acetaldehyde | 0.0285 | 0.0118 | 0.0167 | 58.6 |
| Butyraldehyde | 0.0393 | 0.0026 | 0.0367 | 93.3 |
| Acetic Acid | 0.0554 | 0.0209 | 0.0345 | 62.3 |
| Butyric Acid | 0.0471 | 0.0048 | 0.0423 | 89.8 |
| TOTAL | 5.9615 | 2.3996 | 3.5619 | |

EXAMPLE 5

A mixture as shown in Column II of Table 2 was prepared at room temperature in a well-stirred vessel. To this mixture was added 1.6366 grams of homogeneous palladium olefin oxidation catalyst, containing 0.011 grams of palladium. Specifically, the oxidation catalyst added comprised, 1.3574 grams of $K_5H_4PW_6V_6O_{40}$, 0.2545 grams of $CuSO_4 \cdot 5H_2O$ and 0.0247 grams $PdSO_4 \cdot 2H_2O$. The solution was then allowed to react with 0.2976 grams 1-butene at 30° C. After one hour reaction time, and cooling to room temperature, 17.3640 grams butane solvent was added to extract the oxidation reaction products. The butane-rich phase was analyzed by plasma photo emission spectrometry. The results indicated that only 0.2% of the palladium had been extracted by the butane from the reaction mass. This result shows that substantially all of the palladium remains in the water-rich phase, which, after butane extraction, can be reused for oxidation without further treatment.

TABLE 2

| COMPOSITION (gms) | |
|---|---|
| Water | 30.000 |
| MEK | 2.424 |

TABLE 2-continued

| COMPOSITION (gms) | |
|---|---|
| Acetaldehyde | 0.006 |
| Butyraldehyde | 0.006 |
| Acetic Acid | 0.008 |
| Butyric Acid | 0.006 |
| Sulphuric Acid | 4 Drops of 9N $H_2SO_4$ |

EXAMPLE 6

0.2298 grams of 99.999% pure solid aluminum isopropoxide and 0.0398 grams of zinc chloride were placed under nitrogen in a 60 ml glass flask containing a teflon coated magnetic stir bar. The zinc chloride had previously been dried at 200° C. for hours, to remove any residual moisture. After closing the flask with a sealed septum cap, a solution consisting of 1.6108 grams of n-butyraldehyde, 33.7829 grams of n-heptane solvent and 1.8219 grams of n-hexane internal standard was introduced by syringe. The flask was then placed in an oil bath at 25° C. and the contents of the flask were immediately stirred at about 350 rpm. After 203 minutes of reaction time, a sample of the solution was taken by syringe and analyzed by gas chromatograph. The results revealed that 99.8% of the butyraldehyde had been converted into higher boiling products. The major product was identified as the ester butyl butyrate.

EXAMPLE 7

Example 6 was repeated with methyl ethyl ketone instead of butyraldehyde, to ascertain the specificity of the condensation reaction. In this experiment, 0.2253 grams of pure aluminum isopropoxide and 0.0536 grams of dried zinc chloride were placed under nitrogen in a 60 ml glass flask containing a teflon coated magnetic stir bar. After closing the flask with a sealed septum cap, a solution consisting of 1.6055 grams of methyl ethyl ketone, 30.9547 grams of n-heptane solvent and 0.9617 grams of n-hexane internal standard was introduced by syringe. The flask was then placed in an oil bath at 25° C. and the contents of the flask were immediately stirred at about 350 rpm. After 173 minutes, a sample of the solution was taken by syringe and analyzed by gas chromatograph. The results revealed that no methyl ethyl ketone had been converted.

EXAMPLE 8

Example 6 was repeated using both butyraldehyde and methyl ethyl ketone in the reaction solution, to ascertain that no cross condensation between butyraldehyde and methyl ethyl ketone would occur. In this experiment, 0.2496 grams of aluminum isopropoxide and 0.0347 grams of dried zinc chloride were placed under nitrogen in a 60 ml glass flask containing a teflon coated magnetic stir bar. After closing the flask with a sealed septum cap, a solution consisting of 1.5888 grams of n-butyraldehyde, 1.5496 grams of methyl ethyl ketone, 33.1896 grams of n-heptane solvent and 0.9674 grams of n-hexane internal standard was introduced by syringe. The flask was then placed in an oil bath at 25° C. and stirring immediately started at about 350 rpm. Samples of the reaction solution were analyzed at periodic time intervals, as indicated in Table 3. The results of Table 3 show that, after 122 minutes of reaction time, no methyl ethyl ketone (MEK) has been converted, whereas 92.9% of the butyraldehyde has been converted, primarily into butyl butyrate ester.

TABLE 3

| Reaction time [min] | Concentrations in Solution | | | |
|---|---|---|---|---|
| | Absolute | | Relative* | |
| | MEK [wt. %] | Butyraldehyde [wt. %] | MEK [/] | Butyraldehyde [/] |
| 0 | 4.155 | 4.260 | 1.000 | 1.000 |
| 10 | 4.181 | 3.772 | 1.006 | 0.885 |
| 40 | 4.107 | 1.997 | 0.988 | 0.469 |
| 66 | 4.212 | 1.007 | 1.014 | 0.236 |
| 122 | 4.105 | 0.301 | 0.988 | 0.071 |

*Relative concentrations are defined as the ratio of the concentration in solution at time t and the concentration in solution at time zero. The percentage butyraldehyde conversion at time t is given by 100 minus 100 times the relative butyraldehyde concentration at time t.

EXAMPLE 9

Example 8 was repeated in the absence of n-heptane co-solvent and using an excess amount of methyl ethyl ketone. In this experiment, 0.2610 grams of aluminum isopropoxide and 0.0510 grams of dry zinc chloride were placed under nitrogen in a 60 ml glass flask containing a teflon coated magnetic stir bar. After closing the flask with a sealed septum cap, a solution consisting of 1.4998 grams of n-butyraldehyde, 41.4848 grams of methyl ethyl ketone and 0.6302 grams of n-hexane internal standard was introduced by syringe. The flask was then placed in an oil bath at 25° C. and the contents stirred at about 350 rpm. Samples of the reaction solution were analyzed at periodic time intervals, as indicated in Table 4. The results of Table 4 again reveal that no conversion of the methyl ethyl ketone has taken place even after 45.5 hours of reaction time.

As opposed to the results of Example 6, the butyraldehyde conversion only amounted to 21.0% after 167 minutes, and to 60.7% after 45.5 hours reaction time. The progressive deactivation of the catalyst which is apparent, was concomitant with the formation of a white precipitate in the reaction solution, which was attributed to hydrolysis of the aluminum isopropoxide as evidenced by the appearance of a 2-propanol peak in the gas chromatograph analysis. Knowing that water is much more soluble in methyl ethyl ketone than in n-heptane, and that no efforts had been made to dry the methyl ethyl ketone feed, the differences between the results of Examples 3 and 4 were attributed to contamination of the reaction solution by water.

TABLE 4

| Reaction time [min] | Concentrations in Solution | | | |
|---|---|---|---|---|
| | Absolute | | Relative | |
| | MEK [wt. %] | Butyraldehyde [wt. %] | MEK [/] | Butyraldehyde [/] |
| 0 | 95.119 | 3.436 | 1.000 | 1.000 |
| 10 | 94.464 | 3.374 | 0.993 | 0.982 |
| 38 | 94.576 | 3.264 | 0.994 | 0.950 |
| 70 | 96.415 | 3.187 | 1.014 | 0.927 |
| 107 | 94.668 | 2.941 | 0.995 | 0.856 |
| 167 | 95.493 | 2.715 | 1.004 | 0.790 |
| 1440 | 95.096 | 1.596 | 1.000 | 0.464 |
| 2730 | 95.127 | 1.349 | 1.000 | 0.393 |

EXAMPLE 10

In order to verify the conclusion arrived at in Example 9, the procedure of Example 9 was repeated, but this time using methyl ethyl ketone that had been purified by fractional distillation in order to reduce its water content. In this experiment, 0.2980 grams of aluminum isopropoxide and 0.0393 grams of dried zinc chloride were placed under nitrogen in a 60 ml glass flask containing a teflon coated magnetic stir bar. After closing the flask with a sealed septum cap, a solution consisting of 1.4667 grams of n-butyraldehyde, 37.2653 grams of purified methyl ethyl ketone and 0.3060 grams of n-hexane internal standard was introduced by syringe. The flask was then placed in an oil bath at 25° C. and the contents of the flask were immediately stirred at about 350 rpm. Samples of the reaction solution were analyzed at periodic time intervals, as indicated in Table 5. As compared to the data of Table 4, the data of Table 5 show that the drying of methyl ethyl ketone by distillation resulted in substantially improved butyraldehyde conversion rates. After 180 minutes of reaction time, the butyraldehyde conversion amounted to 67.5%, again at no loss of methyl ethyl ketone.

TABLE 5

| Reaction time [min] | Absolute MEK [wt. %] | Absolute Butyraldehyde [wt. %] | Relative MEK [/] | Relative Butyraldehyde [/] |
|---|---|---|---|---|
| 0 | 95.459 | 3.757 | 1.000 | 1.000 |
| 13.5 | 103.111 | 3.384 | 1.080 | 0.901 |
| 30 | 94.505 | 2.730 | 0.990 | 0.727 |
| 60 | 97.916 | 2.209 | 1.026 | 0.588 |
| 90 | 94.142 | 1.785 | 0.986 | 0.475 |
| 120 | 97.369 | 1.547 | 1.020 | 0.412 |
| 152 | 94.770 | 1.340 | 0.993 | 0.357 |
| 180 | 95.845 | 1.221 | 1.004 | 0.325 |

EXAMPLE 11

Example 10 was repeated at 50° C. instead of 25° C., again using distilled methyl ethyl ketone. In this experiment, 0.2250 grams of aluminum isopropoxide and 0.0455 grams of dried zinc chloride were placed under nitrogen in a 60 ml glass flask containing a teflon coated magnetic stir bar. After closing the flask with a sealed septum cap, a solution consisting of 1.3418 grams of n-butyraldehyde, 26.2086 grams of methyl ethyl ketone and 0.1742 grams of n-hexane internal standard was introduced by syringe. The flask was then placed in an oil bath at 50° C. and the contents of the flask were stirred at about 350 rpm. Samples of the reaction solution were analyzed at periodic time intervals, as summarized in Table 6. The results of Table 6 show that 81.9% of the butyraldehyde has been converted after 3 hours reaction time, at no detectable loss of methyl ethyl ketone. In comparison to the data of Table 5, a 25° C. increase in temperature is shown to increase the butyraldehyde conversion from 67.5% to 81.9% after 180 minutes reaction time.

TABLE 6

| Reaction time [min] | Concentrations in solution MEK [wt. %] | Butanal [wt. %] | MEK [/] | Butanal [/] |
|---|---|---|---|---|
| 0 | 95.937 | 3.425 | 1.000 | 1.000 |
| 11 | 97.244 | 2.137 | 1.014 | 0.624 |
| 38 | 95.646 | 1.287 | 0.997 | 0.376 |
| 60 | 96.080 | 1.042 | 1.001 | 0.304 |
| 90 | 96.633 | 0.856 | 1.007 | 0.250 |
| 120 | 95.713 | 0.751 | 0.998 | 0.219 |
| 150 | 98.729 | 0.650 | 1.029 | 0.190 |
| 180 | 100.076 | 0.620 | 1.043 | 0.181 |

EXAMPLE 12

Example 10 was repeated at 100° C. instead of 25° C., again using distilled methyl ethyl ketone. In this experiment, 0.2600 grams of aluminum isopropoxide and 0.0400 grams of dried zinc chloride were placed under nitrogen in a 60 ml glass flask containing a teflon coated magnetic stir bar. After closing the flask with a sealed septum cap, a solution consisting of 1.5895 grams of n-butyraldehyde, 42.3720 grams of methyl ethyl ketone and 0.2305 grams of n-hexane internal standard was introduced by syringe. The flask was then placed in an oil bath at 100° C. and the contents of the flask were immediately stirred at about 350 rpm. After 70 minutes of reaction time, no methyl ethyl ketone had been converted and the conversion of butyraldehyde amounted to 56.7%. Butyraldehyde appeared to be converted into several higher boiling products, including butyl butyrate ester and n-butanol, possibly indicating catalyst decomposition at this higher operating temperature. The presence of n-butanol in the products moreover indicates that there might still have been residual water in the feed, despite the use of distilled methyl ethyl ketone. A comparison of the results of Examples 5, 6 and 7 suggests that the optimum temperature for achieving high butyraldehyde reaction rates with this catalyst system lies between 25° C. and 100° C.

EXAMPLE 13

Example 12 was repeated, this time however allowing the alkoxide catalyst and zinc chloride promotor to soak for 1 hour in distilled methyl ethyl ketone at 100° C., prior to introduction of the n-butyraldehyde and n-hexane standard. The procedure of this experiment was as follows. 0.2701 grams of aluminum isopropoxide, 0.0398 grams of dried zinc chloride and 43.8838 grams of methyl ethyl ketone were placed under nitrogen in a 60 ml glass flask containing a teflon coated magnetic stir bar. After closing the flask with a sealed septum cap, the flask was placed in an oil bath at 100° C. and the contents of the flask were stirred for one hour. After that, while still at temperature, a solution consisting of 1.2325 grams of n-butyraldehyde and 0.2055 grams of n-hexane internal standard was introduced by syringe, while stirring was continued. Samples of the reaction solution were taken at periodic intervals, as summarized in Table 7. The results of Table 7 show that only 21.6% of the butyraldehyde was converted, but at no detectable loss of methyl ethyl ketone. The gas chromatograph analysis of the products revealed that several higher boiling products had been made, among which were butyl butyrate and n-butanol.

TABLE 7

| Reaction time [min] | Absolute MEK [wt. %] | Absolute Butyraldehyde [wt. %] | Relative MEK [/] | Relative Butyraldehyde [/] |
|---|---|---|---|---|
| 0 | 96.827 | 2.719 | 1.000 | 1.000 |
| 17 | 96.827 | 2.459 | 1.000 | 0.904 |
| 48 | 98.027 | 2.296 | 1.012 | 0.844 |
| 75 | 93.778 | 2.111 | 0.969 | 0.776 |
| 106 | 96.989 | 2.132 | 1.002 | 0.784 |

EXAMPLE 14

Example 11 was repeated using aluminum tertiary butoxide instead of aluminum isopropoxide as a catalyst, again using distilled methyl ethyl ketone. In this experiment, 0.2341 grams of aluminum tertiary butoxide and 0.0464 grams of dried zinc chloride were placed under nitrogen in a 60 ml glass flask containing a teflon coated magnetic stir bar. After closing the flask with a sealed septum cap, a solution consisting of 1.7832 grams of butyraldehyde, 39.7766 grams of methyl ethyl ketone and 0.3936 grams of n-hexane internal standard was introduced by syringe. The flask was then placed in an oil bath at 50°° C. and the contents of the flask were immediately stirred at about 350 rpm. Samples of the reaction solution were analyzed at periodic time intervals, as indicated in Table 8. The results of Table 8 show a butyraldehyde conversion of 85.5% after 130 minutes of reaction time, at no detectable loss of methyl ethyl ketone. The products of the butyraldehyde conversion consisted of butyl butyrate (69.6%), n-butanol (23.8%) and secondary butyl alcohol (6.5%).

TABLE 8

| Reaction time [min] | Concentrations in Solution | | | |
|---|---|---|---|---|
| | Absolute | | Relative | |
| | MEK [wt. %] | Butyraldehyde [wt. %] | MEK [/] | Butyraldehyde [/] |
| 0 | 94.811 | 4.250 | 1.000 | 1.000 |
| 10 | 93.642 | 3.750 | 0.988 | 0.882 |
| 42 | 91.756 | 1.452 | 0.968 | 0.342 |
| 71 | 96.385 | 1.031 | 1.017 | 0.242 |
| 100 | 96.305 | 0.801 | 1.016 | 0.188 |
| 130 | 94.544 | 0.617 | 0.997 | 0.145 |

EXAMPLE 15

Example 11 was repeated using liquid zinc isopropoxide instead of aluminum isopropoxide as a catalyst, and in the absence of zinc chloride. In this experiment, 0.4068 grams of zinc isopropoxide was placed under nitrogen in a 60 ml glass flask containing a teflon coated magnetic stir bar. After closing the flask with a sealed septum cap, a solution consisting of 1.6942 grams of n-butyraldehyde, 37.4425 grams of methyl ethyl ketone and 0.2289 grams of n-hexane internal standard was introduced by syringe. The flask was then placed in an oil bath at 50° C. and the contents of the flask were immediately stirred at about 350 rpm. Samples of the reaction solution were analyzed at periodic time intervals, as indicated in Table 9. The conversion of butyraldehyde amounted to 53.1% after 100 minutes of reaction time.

TABLE 9

| Reaction time [min] | Concentrations in Solution | | | |
|---|---|---|---|---|
| | Absolute | | Relative | |
| | MEK [wt. %] | Butyraldehyde [wt. %] | MEK [/] | Butyraldehyde [/] |
| 0 | 95.115 | 4.304 | 1.000 | 1.000 |
| 10 | 96.550 | 3.084 | 1.015 | 0.717 |
| 40 | 91.369 | 2.430 | 0.961 | 0.565 |
| 70 | 93.192 | 2.149 | 0.980 | 0.499 |
| 100 | 96.072 | 2.020 | 1.010 | 0.469 |

EXAMPLE 16

Methyl ethyl ketone was purified by slow fractional distillation, followed by storage over activated molecular sieve 3A for 24 hrs, in an attempt to further improve the dryness of the methyl ethyl ketone used. Prior to use, the molecular sieve had been activated at 300° C. for 48 hours. The methyl ethyl ketone was then used in the following experiment, with substantially the same procedure of Example 11. 0.2378 grams of aluminum isopropoxide and 0.0573 grams of dry zinc chloride were placed under nitrogen in a 60 ml glass flask containing a teflon coated magnetic stir bar. After closing the flask with a sealed septum cap, a solution consisting of 1.4520 grams of n-butyraldehyde, 36.7935 grams of methyl ethyl ketone and 0.3780 grams of n-hexane internal standard was introduced by syringe. The flask was then placed in an oil bath at 50° C. and the contents of the flask were stirred at about 350 rpm. Samples of the reaction solution were analyzed at periodic time intervals, as indicated in Table 10. The results of Table 10 show that 88.5% of the butyraldehyde has been converted into higher boiling products after 163 minutes reaction time, at no detectable loss of methyl ethyl ketone. A comparison with the data of Table 6 shows that a more thorough drying of the methyl ethyl ketone has further improved the catalyst activity.

TABLE 10

| Reaction time [min] | Concentrations in Solution | | | |
|---|---|---|---|---|
| | Absolute | | Relative | |
| | MEK [wt. %] | Butyraldehyde [wt. %] | MEK [/] | Butyraldehyde [/] |
| 0 | 95.262 | 3.759 | 1.000 | 1.000 |
| 10 | 91.854 | 2.263 | 0.964 | 0.602 |
| 40 | 97.722 | 0.828 | 1.026 | 0.220 |
| 70 | 95.772 | 0.642 | 1.005 | 0.171 |
| 100 | 93.263 | 0.522 | 0.979 | 0.139 |
| 130 | 94.754 | 0.424 | 0.995 | 0.113 |
| 163 | 96.375 | 0.434 | 1.012 | 0.115 |

EXAMPLE 17

Example 16 was repeated, but this time in the absence of zinc chloride promoter. Thus, 0.2728 grams of aluminum isopropoxide was placed under nitrogen in a 60 ml glass flask containing a teflon coated magnetic stir bar. After closing the flask with a sealed septum cap, a solution consisting of 1.5178 grams of n-butyraldehyde, 34.7936 grams of methyl ethyl ketone and 0.5273 grams of n-hexane internal standard was introduced by syringe. The flask was then placed in an oil bath at 50° C. and the contents of the flask were stirred at about 350 rpm. After 40 minutes reaction time, the butyraldehyde conversion only amounted to 41.4%, as opposed to 78.0% under the conditions of Example 16.

EXAMPLE 18

Example 16 was repeated using the same purified methyl ethyl ketone feed source, but at the following different loadings. Thus, 0.2589 grams of aluminum isopropoxide and 0.0326 grams of dry zinc chloride were placed under nitrogen in a 60 ml glass flask containing a teflon coated magnetic stir bar. After closing the flask with a sealed septum cap, a solution consisting of 0.5112 grams of n-butyraldehyde, 37.5153 grams of methyl ethyl ketone and 0.4353 grams of n-hexane internal standard was introduced by syringe. The flask was then placed in an oil bath at 50° C. and the contents of the flask were stirred at about 350 rpm. The conversion of butyraldehyde amounted to 96.7% after 70 minutes reaction time.

EXAMPLE 19

Example 16 was repeated using liquid aluminum secondary butoxide instead of aluminum, isopropoxide as a catalyst, with the same purified methyl ethyl ketone feed source. In this experiment, 0.2580 grams of aluminum secondary butoxide and 0.0519 grams of dry zinc chloride were placed under nitrogen in a 60 ml glass flask containing a teflon coated magnetic stir bar. After closing the flask with a sealed septum cap, a solution consisting of 0.5961 grams of n-butyraldehyde, 38.3602 grams of methyl ethyl ketone and 0.4760 grams of n- hexane internal standard was introduced by syringe. The flask was then placed in an oil bath at 50° C. and the contents of the flask were stirred at about 350 rpm. The butyraldehyde conversion amounted to 93.3% after 160 minutes reaction time, at no detectable loss of methyl ethyl ketone.

We claim:

1. A method for removing aldehydes from a mixture of aldehydes and ketones which comprises the steps of:
    (a) providing to a reactor a substantially water-free mixture of aldehydes and ketones;
    (b) providing to said reactor a Tischtschenko catalyst selected from the group consisting of multi-valent metal alkoxides of the form $[M(OR)_n]$, where M is a Group IIB, Group IIIA or Group IVB metal, R is an alkyl group, and n is equal to the valence state of metal M;
    (c) contacting said substantially water-free aldehyde and ketone mixture with said provided Tischtschenko catalyst to thereby condense said aldehydes into esters, wherein said esters have a boiling point significantly different from said ketone; and,
    (d) separating said esters and Tischtschenko catalyst from said ketone mixture.

2. The method of claim 1 wherein said ketone is selected from the group consisting of acetone, methyl ethyl ketone and methyl isobutyl ketone.

3. The method of claim 1 wherein said Tischtschenko catalyst is selected from the group consisting of aluminum isopropoxide, aluminum butoxide, aluminum ethoxide and titanium ethoxide.

4. The method of claim 1 wherein said esters are separated from said ketone mixture by thermal distillation.

5. The method of claim 1 further comprising the step of providing to said reactor, prior to step (c), a promoter selected from the group consisting of metal chlorides of the form $M'Cl_m$, wherein M' is a Group II or Group IIIA metal, and m is equal to the valence state of metal M', and further, in step (d), separating said promoter from said ketone mixture.

6. The method of claim 5 wherein said promoter is selected from the group consisting of $ZnCl_2$, $HgCl_2$, $CaCl_2$ and $AlCl_3$.

7. A method for removing water and aldehydes from a mixture of water, aldehydes and ketones which comprises the steps of:
    (a) providing a crude ketone stream containing water, aldehydes and ketones;
    (b) contacting said provided crude ketone stream with an extraction solvent to obtain an organic extractant phase containing the extraction solvent, aldehydes, ketones and trace quantities of water, and an aqueous raffinate phase containing the water and water-soluble components of the crude ketone stream;
    (c) thermally, fractionally distilling said organic extractant phase to obtain at least an extraction solvent fraction and a dry ketone fraction containing aldehydes with boiling points relatively close to the boiling points of said ketones;
    (d) providing to a reactor a Tischtschenko catalyst selected from the group consisting of multivalent metal alkoxides of the from $[M(OR)_n]$, wherein M is a Group IIB, Group IIIA or Group IVB metal, R is an alkyl group, and n is equal to the valence state of metal M;
    (e) contacting said dry ketone phase with said Tischtschenko catalyst in said reactor to thereby condense said aldehydes into esters, wherein said esters have a boiling point significantly different from said ketone; and,
    (f) separating said esters and Tischtschenko catalyst from said ketone phase.

8. The method of claim 7 wherein said ketone is selected from the group consisting of acetone, methyl ethyl ketone and methyl isobutyl ketone.

9. The method of claim 7 wherein said Tischtschenko catalyst is selected from the group consisting of aluminum isopropoxide, aluminum butoxides, aluminum ethoxide and titanium ethoxide.

10. The method of claim 7 further comprising the step of providing to said reactor, prior to step (e), a promoter selected from the group consisting of metal chlorides of the form $M'Cl_m$, wherein M' is a Group II or Group IIIA metal, and m is equal to the valance state of metal M', and further in step (f), separating said promoter from said ketone phase.

11. The method of claim 10 wherein said promoter is selected from the group consisting of $ZnCl_2$, $HgCl_2$, $CaCl_2$ and $AlCl_3$.

12. The method of claim 7 wherein said esters are separated from said ketone phase, in step (f), by thermal distillation.

13. The method of claim 7 wherein said extraction solvent, in step (b), is selected from the group consisting of butane, pentane, hexane, heptane, octane, nonane, decane and mixtures thereof.

14. The method of claim 7 wherein said ketone is methyl ethyl ketone and said extraction solvent, in step (b), is butane.

15. A process for obtaining high purity ketone products from olefins through aqueous phase catalyzed olefin oxidation which process comprises the steps of:
    (a) providing an olefin feed stream to an oxidation reactor;
    (b) providing an oxygen-containing stream to said oxidation reactor;
    (c) providing an aqueous catalyst stream to said oxidation reactor;
    (d) combining said provided streams to form an oxidation reaction mass;
    (e) maintaining said oxidation reaction mass in a well-mixed state in said oxidation reactor to obtain a ketone crude which comprises desired ketone products, olefin oxidation byproducts and unreacted olefin feed components dissolved in, or mixed with, said aqueous catalyst phase;
    (f) contacting said ketone crude with an extraction solvent to form two liquid phases, a first substantially catalyst-free organic extractant phase which contains said desired ketone products, olefin oxidation byproducts and said extraction solvent and a second, catalyst-containing aqueous raffinate phase;
    (g) recycling said second catalyst-containing aqueous raffinate phase to said olefin oxidation reactor;
    (h) recovering an anhydrous ketone-rich stream from said first catalyst-free organic extractant phase; and,
    (i) contacting said anhydrous ketone-rich stream, with a Tischtschenko catalyst selected from the group consisting of multivalent metal alkoxides of the form $[M(OR)_n]$ wherein M is a Group IIB, Group IIIA or Group IVB metal, R is an alkyl group, and n is equal to the valence state of metal M, to thereby condense aldehydic impurities in said anhydrous ketone product into ester products wherein said ester products have a boiling point significantly different from said ketone; and, (j) separating said Tischtschenko catalyst, said ester products, and said olefin oxidation byproducts from said anhydrous ketone-rich stream to obtain a high purity ketone product.

16. The process of claim 15 wherein said extraction solvent in step (f) is selected from the group consisting of butane, pentane, hexane, heptane, octane, nonane, decane and mixtures thereof.

17. The process of claim 15 wherein said olefin feed is butene, said desired ketone product is methyl ethyl ketone and said extraction solvent is butane.

18. The process of claim 15 wherein said extraction solvent in step (f) is a component of said olefin feed.

19. The process of claim 15 further comprising: removing unreacted olefin feed components present in said ketone crude prior to step (f).

20. The process of claim 15 further comprising: depressurizing said ketone crude to remove unreacted olefin feed components, prior to step (f).

21. The process of claim 15 wherein said Tischtschenko catalyst is selected from the group consisting of aluminum isopropoxide, aluminum butoxides, aluminum ethoxide, and titanium ethoxide.

22. The process of claim 15 wherein during step (i) said anhydrous ketone product is simultaneously contacted with a promoter selected from the group of metal chlorides of the from $M'Cl_m$ wherein M' is a Group II or Group IIIA metal and m is equal to the valence state of metal M', and where, during step (j) said promoter is separated from said anhydrous ketone product.

23. The process claim 22 wherein said promoter is selected from the group consisting of $ZnCl_2$, $HgCl_2$, $CaCl_2$ and $AlCl_3$.

24. A process for obtaining high purity ketone products from olefins through aqueous phase catalyzed olefin oxidation which process comprises the steps of:

(a) providing an olefin feed stream to an oxidation reactor;

(b) providing an oxygen-containing stream to said oxidation reactor;

(c) providing an aqueous catalyst stream to said oxidation reactor;

(d) combining said provided streams to form an oxidation reaction mass;

(e) maintaining said oxidation reaction mass in a well-mixed state in said oxidation reactor to obtain a ketone crude which comprises desired ketone products, olefin oxidation byproducts and unreacted olefin feed components dissolved in, or mixed with, said aqueous catalyst phase;

(f) contacting said ketone crude with an extraction solvent to form two liquid phases, a first substantially catalyst-free organic extractant phase which contains said desired ketone products, oxidation byproducts and said extraction solvent and a second, catalyst-containing aqueous raffinate phase, said extraction solvent characterized in having a boiling point lower than the boiling point of said desired ketone products;

(g) recycling said catalyst-containing aqueous raffinate phase to said olefin oxidation reactor;

(h) recovering said extraction solvent and low boiling oxidation reaction byproducts as an overhead stream in a thermal distillation of said first, substantially catalyst-free organic extractant phase and obtaining as a bottoms product a substantially anhydrous ketone-enriched stream containing said desired ketone products and higher boiling olefin oxidation byproducts;

(i) removing the balance of the low boiling oxidation byproducts to recover a substantially anhydrous ketone product from said substantially anhydrous ketone-enriched stream;

(j) contacting said substantially anhydrous ketone product with a Tischtschenko catalyst selected from the group consisting of multivalent metal alkoxides of the form $[M(OR)_n]$, wherein M is a Group IIB, Group IIIA or Group IVB metal, R is an alkyl group, and n is equal to the valance state of metal M, to thereby condense aldehydic impurities in said substantially anhydrous ketone product into ester products, wherein said ester products have a boiling point significantly different from said ketone; and, (k) separating said Tischtschenko catalyst, high boiling oxidation reaction byproducts and said ester products from said substantially anhydrous ketone product to obtain a high purity ketone product.

25. The process of claim 24 wherein said extraction solvent is step (f) is selected from the group consisting of butane, pentane, hexane, heptane, octane, nonane, decane and mixtures thereof.

26. The process of claim 24 wherein said olefin feed is butene, said desired ketone product is methyl ethyl ketone and said extraction solvent is butane.

27. The process of claim 24 wherein said extraction solvent is step (f) is a component of said olefin feed.

28. The process of claim 24 further comprising: removing unreacted olefin feed components present in said ketone crude prior to step (f).

29. The process of claim 24 further comprising: depressuring said ketone crude to remove unreacted olefin feed components prior to step (f).

30. The process of claim 24 wherein said Tischtschenko catalyst is selected from the group consisting of aluminum isopropoxide, aluminum butoxides, aluminum ethoxide, and titanium ethoxide.

31. The process of claim 24 wherein during step (j), said substantially anhydrous ketone product is simultaneously contacted with a promoter selected from the group of metal chlorides of the form $M'CLhd m$ wherein M' is a Group II or Group IIIA metal, and m is equal to the valence state of metal M', and wherein, during step (k), said promoter is separated from said anhydrous ketone product.

32. The process of claim 31 wherein said promoter is selected from the group consisting of $ZnCl_2$, $HgCl_2$, $CaCl_2$ and $AlCl_3$.

33. A process for obtaining high purity ketone products from olefins through aqueous phase catalyzed olefin oxidation which process comprises the steps of:

(a) providing an olefin feed stream to an oxidation reactor;

(b) providing an oxygen-containing stream to said oxidation reactor;

(c) providing an aqueous catalyst stream to said oxidation reactor;

(d) combining said provided streams to form an oxidation reaction mass;

(e) maintaining said oxidation reaction mass in a well-mixed state in said oxidation reactor to obtain a ketone crude which comprises desired ketone products, olefin oxidation byproducts and unreacted olefin feed components dissolved in, or mixed with said aqueous catalyst phase;

(f) contacting said ketone crude with an extraction solvent to form two liquid phases, a first, substantially catalyst-free organic extractant phase which contains said desired ketone products, oxidation byproducts and said extraction solvent and a second, catalyst-containing aqueous raffinate phase, said extraction solvent characterized in having a boiling point higher than the boiling point of said desired ketone product;

(g) recycling said second, catalyst-containing aqueous raffinate phase to said olefin oxidation reactor;

(h) thermally distilling said first, substantially catalyst-free organic phase to remove low boiling oxidation byproducts and dissolved water as an overhead product to obtain a substantially anhydrous ketone-enriched extraction solvent stream;

(i) contacting said substantially anhydrous ketone-enriched extraction solvent stream with a Tischtschenko catalyst selected from the group consisting of multivalent metal alkoxides of the form $[M(OR)_n]$, wherein M is a Group IIB, Group IIIA or Group IVB metal, R is an alkyl group, and n is equal to the valance state of metal M, to thereby condense aldehydic impurities in said substantially anhydrous ketone-enriched extraction solvent stream into ester products wherein said ester products have a boiling point significantly different from said ketone; and, (j) recovering substantially pure, anhydrous ketone product from said substantially anhydrous, ketone-enriched extraction solvent stream; and (k) recovering said extraction solvent from said substantially anhydrous, ketone-enriched, aldehyde-free extraction solvent stream for recycle to said solvent-ketone crude contacting step (f) by removing high boiling oxidation byproducts, other high boiling impurities and Tischtschenko catalyst.

34. The process of claim 33 wherein said extraction solvent is selected from the group consisting of heptane, octane, nonane, decane and mixtures thereof.

35. The process of claim 33 further comprising: removing unreacted olefin feed components present in said ketone crude prior to step (f).

36. The process of claim 33 further comprising: depressurizing said ketone crude to remove unreacted olefin feed components prior to step (f).

37. The process of claim 33 wherein said Tischtschenko catalyst is selected from the group consisting of aluminum isopropoxide, aluminum butoxides, aluminum ethoxide and titanium ethoxide.

38. The process of claim 33 wherein during step (i), said substantially anhydrous ketone product is simultaneously contacted with a promoter selected from the group of metal chlorides of the form $M'Cl_m$ wherein $M'$ is a Group II or Group IIIA metal, and m is equal to the valence state of metal $M'$, and wherein during step (k), said promoter is separated from said substantially anhydrous, ketone-enriched, aldehyde-free extraction solvent steam.

39. The process of claim 38 wherein said promoter is selected from the group consisting of $ZnCl_2$, $HgCl_2$, $CaCl_2$ and $AlCl_3$.

40. A process for obtaining high purity ketone product from olefins through aqueous phase, transition-metal-catalyzed olefin oxidation comprising the steps of:

(a) providing an olefin feed stream to an oxidation reactor;

(b) providing an oxygen-containing stream to said oxidation reactor;

(c) providing an aqueous catalyst stream to said oxidation reactor;

(d) combining said provided streams to form an oxidation reaction mass;

(e) maintaining said oxidation reaction mass in a well-mixed state in said oxidation reactor to obtain a ketone crude which comprises desired ketone products, olefin oxidation byproducts and unreacted olefin feed components, dissolved in, or mixed with said aqueous catalyst phase;

(f) depressurizing said ketone crude to separate as an overhead product unreacted olefin feed components, desired ketone products, olefin oxidation byproducts and some water from said aqueous oxidation catalyst;

(g) contacting said depressurized wet ketone crude overhead product with an extraction solvent to form two liquid phases, a first substantially dry organic extractant phase which contains said desired ketone products, oxidation byproducts and the extraction solvent and a second aqueous raffinate phase;

(h) recovering substantially anhydrous ketone product from said first, substantially dry extractant phase;

(i) contacting said substantially anhydrous ketone product with a Tischtschenko catalyst selected from the group consisting of multivalent metal alkoxides of the form $[M(OR)_n]$ wherein M is a Group IIB, Group IIIA or Group IVB metal R is an alkyl group, and n is equal to the valance state of metal M, to thereby condense aldehydic impurities in said substantially anhydrous ketone product into ester products wherein said ester products have a boiling point significantly different from said ketone; and, (j) separating said Tischtschenko catalyst, said ester products, and olefin oxidation byproducts from said substantially anhydrous ketone products to obtain high purity ketone products.

41. The process of claim 40 wherein said extraction solvent is selected from the group consisting of butane, pentane, hexane, heptane, octane, nonane, decane and mixtures thereof.

42. The process of claim 40 wherein said olefin feed is butene, said desired ketone product is methyl ethyl ketone and said extraction solvent is butane.

43. The process of claim 40 wherein said extraction solvent is a component of said olefin feed stream.

44. The process of claim 40 wherein the step of recovering substantially anhydrous ketone product from said first substantially dry extractant phase consists essentially of:

thermally distilling said first substantially dry organic phase to obtain a substantially anhydrous ketone-enriched organic phase.

45. The process of claim 40 wherein said Tischtschenko catalyst is selected from the group consisting of aluminum isopropoxide, aluminum butoxides, aluminum ethoxide and titanium ethoxide.

46. The process of claim 40 wherein during step (i), said substantially anhydrous ketone product is simultaneously contacted with a promoter selected from the group of metal chlorides of the form $M'Cl_m$ wherein M' is a Group II or Group IIIA metal, and m is equal to the valence state of metal M', and wherein during step (j), said promoter is separated from said substantially anhydrous ketone product.

47. The process of claim 45 wherein said promoter is selected from the group consisting of $ZnCl_2$, $HgCl_2$, $CaCl_2$ and $AlCl_3$.

48. A process for obtaining a ketone product, substantially free of aldehydic impurities, which comprises the steps of:
   (a) providing a ketone crude stream containing a desired ketone product and undesired reaction byproducts including aldehydic impurities whose boiling points are substantially similar to the boiling point of said desired ketone product, thereby making thermal distillation an inefficient method of separating said aldehydic impurities from said desired ketone product;
   (b) treating said ketone crude stream to remove substantially all of the water present in said ketone crude stream to obtain an anhydrous ketone crude stream;
   (c) contacting said anhydrous ketone crude stream with a Tischtschenko catalyst selected from the group consisting of multivalent metal alkoxides of the form $[M(OR)_n]$ wherein M is a Group IIB, Group IIIA or Group IVB metal, R is an alkyl group, and n is equal to the valence state of metal M to thereby condense said aldehydic impurities in said anhydrous ketone crude stream into ester products whose boiling points are significantly different than said desired ketone product; and,
   (d) separating said Tischtschenko catalyst and said ester products from said anhydrous ketone crude stream, to obtain a ketone product substantially free of aldehydic impurities.

49. The process of claim 48 wherein said Tischtschenko catalyst is selected from the group consisting of aluminum isopropoxide, aluminum butoxides, aluminum ethoxide, and titanium ethoxide.

50. The process of claim 48 wherein during step (c), said anhydrous ketone crude stream is simultaneously contacted with a promoter selected from the group of metal chlorides of the form $M'Cl_m$ is a Group II or Group IIIA metal, and m is equal to the valence state of metal M', and wherein during step (d), said promoter is separated from said anhydrous ketone crude stream.

51. The process of claim 50 wherein said promoter is selected from the group consisting of $ZnCl_2$, $HgCl_2$, $CaCl_2$ and $AlCl_3$.

52. A process for obtaining high purity ketone products from olefins through aqueous phase catalyzed olefin oxidation which process comprises the steps of:
   (a) providing an olefin feed stream to a first reactor;
   (b) providing an aqueous catalyst stream to said first reactor, said catalyst in its oxidized state;
   (c) combining said provided olefin feed stream and said aqueous catalyst stream in said first reactor and maintaining said olefin feed stream and aqueous catalyst stream in a well-mixed state to obtain a ketone crude which comprises desired ketone products, olefin oxidation byproducts and unreacted olefin feed components dissolved in, or mixed with, said aqueous catalyst, said catalyst now in a reduced state;
   (d) depressurizing said ketone crude to separate as an overhead product unreacted olefin components, desired ketone products and olefin oxidation byproducts from said aqueous oxidation catalyst in a reduced state;
   (e) providing said reduced oxidation catalyst to a second reactor;
   (f) providing an oxygen-containing stream to said second reactor;
   (g) maintaining said reduced oxidation catalyst and said oxygen-containing stream in a well-mixed state in said second reactor to thereby reoxidize the catalyst;
   (h) recycling said reoxidized catalyst to step (b);
   (i) treating said flashed overhead product from step (d) by extraction and distillation to obtain a substantially dry ketone-containing stream;
   (j) contacting said substantially dry ketone-containing stream with a Tischtschenko catalyst selected from the group consisting of multivalent metal alkoxides of the form $[M(OR)_n]$ wherein M is a Group IIB, Group IIIA or Group IVB metal, R is an alkyl group and n is equal to the valence state of metal M to thereby condense aldehydic impurities in said substantially dry ketone-containing stream into ester products, wherein said ester products have a boiling point significantly different from said ketone; and,
   (k) separating said Tischtschenko catalyst and said ester products from said substantially dry ketone-containing stream to obtain a substantially pure ketone product.

53. The process of claim 52 wherein said olefin feed is butene and said ketone product is methyl ethyl ketone.

54. The process of claim 52 wherein said Tischtschenko catalyst is selected from the group consisting of aluminum isopropoxide, aluminum butoxides, aluminum ethoxide and titanium ethoxide.

55. The process of claim 52 wherein during step (j), said substantially dry, ketone-containing stream is simultaneously contacted with a promoter selected from the group of metal chlorides of the form $M'Cl_m$ wherein M' is a Group II or Group IIIA metal, and m is equal to the valence state of metal M', and wherein during step (j), said promoter is separated from said substantially dry, ketone-containing stream.

56. The process of claim 55 wherein said promoter is selected from the group consisting of $ZnCl_2$, $HgCl_2$, $CaCl_2$ and $AlCl_3$.

57. A process for obtaining high purity ketone products from olefins through aqueous phase catalyzed olefin oxidation which process comprises the steps of:
   (a) providing an olefin feed stream to a first reactor;
   (b) providing an aqueous catalyst stream to said first reactor, said catalyst in its oxidized state;
   (c) combining said provided olefin feed stream and said aqueous catalyst stream in said first reactor and maintaining said olefin stream and aqueous catalyst stream in a well-mixed state to obtain a ketone crude which comprises desired ketone products, olefin oxidation byproducts and unreacted olefin feed components dissolved in, or mixed with, said aqueous catalyst, now in a reduced state;
   (d) contacting said ketone crude with an extraction solvent to form two liquid phases, a first substantially catalyst-free organic extractant phase which contains said desired ketone products, olefin oxidation byproducts and said extraction solvent and a second, catalyst containing raffinate phase, said catalyst in a reduced state;

(e) providing said reduced catalyst-containing raffinate phase to a second reactor;

(f) providing an oxygen-containing stream to said second reactor;

(g) maintaining said reduced catalyst-containing raffinate phase and said oxygen-containing stream in a well-mixed state in said second reactor to thereby reoxidize the catalyst;

(h) receiving said reoxidized catalyst to step (d);

(i) obtaining a substantially dry ketone-containing stream from said organic extractant phase from step (g);

(j) contacting said substantially dry ketone-containing stream with a Tischtschenko catalyst selected from the group consisting of multivalent metal alkoxides of the form $[M(OR)_n]$ wherein M is a Group IIB, Group IIIA or Group IVB metal, R is an alkyl group and n is equal to the valence state of metal M to thereby condense aldehydic impurities in said substantially dry ketone-containing stream into ester products, wherein said ester products have a boiling point significantly different from said ketone; and, (k) separating said Tischtschenko catalyst, olefin oxidation byproducts and said ester products from said substantially aldehyde-free, dry ketone-containing stream to obtain a substantially pure ketone product.

58. The process of claim 57 wherein said olefin feed is butene and said ketone product is methyl ethyl ketone.

59. The process of claim 57 wherein said Tischtschenko catalyst is selected from the group consisting of aluminum isopropoxide, aluminum butoxides, aluminum ethoxide and titanium ethoxide.

60. The process of claim 57 wherein during step (j) said substantially dry ketone-containing stream is simultaneously contacted with a promoter selected from the group of metal chlorides of the form $M'Cl_m$ wherein M' is a Group II or Group IIIA metal, and m is equal to the valence state of metal M', and wherein during step (k), said promoter is separated from said substantially dry ketone-containing stream.

61. The process of claim 60 wherein said promoter is selected from the group consisting of $ZnCl_2$, $HgCl_2$, $CaCl_2$ and $AlCl_3$.

62. The process of claim 57 wherein said alkane extraction solvent is selected from the group consisting of butane, pentane, hexane, heptane, octane, nonane, decane and mixtures thereof.

* * * * *